United States Patent
Lobl et al.

(10) Patent No.: US 8,267,905 B2
(45) Date of Patent: Sep. 18, 2012

(54) APPARATUS AND METHOD FOR DELIVERY OF THERAPEUTIC AND OTHER TYPES OF AGENTS

(75) Inventors: Thomas J. Lobl, Valencia, CA (US); Stephen J. McCormack, Claremont, CA (US); Anna Imola Nagy, Valencia, CA (US); Jacob E. Pananen, Los Angeles, CA (US); John V. Schloss, Valencia, CA (US)

(73) Assignee: NeuroSystec Corporation, Valencia, CA (US)

( * ) Notice: Subject to any disclaimer, the term of this patent is extended or adjusted under 35 U.S.C. 154(b) by 1659 days.

(21) Appl. No.: 11/414,543

(22) Filed: May 1, 2006

(65) Prior Publication Data

US 2007/0255237 A1    Nov. 1, 2007

(51) Int. Cl.
*A61M 31/00* (2006.01)
*A61M 37/00* (2006.01)
*A61K 9/22* (2006.01)

(52) U.S. Cl. ............. 604/288.01; 604/890.1; 604/891.1; 604/892.1

(58) Field of Classification Search ............. 604/288.01, 604/506, 117, 890.1, 891.1, 892.1; 607/137, 607/120, 55; 424/427, 489, 409, 408, 404, 424/400, 422; 514/325
See application file for complete search history.

(56) References Cited

U.S. PATENT DOCUMENTS

| | | | |
|---|---|---|---|
| 3,894,538 A | 7/1975 | Richter | |
| 4,034,756 A | 7/1977 | Higuchi et al. | |
| 4,360,019 A | 11/1982 | Portner et al. | |
| 4,487,603 A | 12/1984 | Harris | |
| 4,511,355 A | 4/1985 | Franetzki et al. | |
| 4,639,244 A | 1/1987 | Rizk et al. | |
| 4,692,147 A | 9/1987 | Duggan | |
| 4,725,852 A | 2/1988 | Gamblin et al. | |
| 4,819,647 A | 4/1989 | Byers et al. | |
| 4,929,236 A | 5/1990 | Sampson | |
| 4,944,659 A | 7/1990 | Labbe et al. | |
| 5,041,107 A | 8/1991 | Heil | |

(Continued)

FOREIGN PATENT DOCUMENTS

DE    3713061    11/1987

(Continued)

OTHER PUBLICATIONS

Gould, et al., International Journal of Pharmaceutics, 33 (1986), pp. 201-217.

(Continued)

*Primary Examiner* — Kevin C Sirmons
*Assistant Examiner* — Michael J Anderson
(74) *Attorney, Agent, or Firm* — Banner & Witcoff, Ltd.

(57) ABSTRACT

Implantable drug delivery systems target delivery of small volumes of drugs to specific tissues. In some cases, a drug delivery system includes an implantable osmotic pump connected to a drug-containing housing, with that housing connected to a needle, cochlear implant or other type of component for ultimate delivery to the target tissue. In some implementations, a subcutaneous port receives a fluid from an external pump. The port is connected to a needle or other component for delivery of one or more drugs to the target tissue. Both solid and liquid drug formulations can be used. In embodiments using solid drugs, a separate drug vehicle (such as saline) can be used to dissolve a portion of the solid drug, with the drug-loaded vehicle then delivered to the target tissue.

10 Claims, 12 Drawing Sheets

U.S. PATENT DOCUMENTS

| | | | |
|---|---|---|---|
| 5,207,640 A | 5/1993 | Hattler | |
| 5,354,279 A | 10/1994 | Hofling | |
| 5,421,818 A * | 6/1995 | Arenberg | 604/21 |
| 5,441,481 A | 8/1995 | Mishra et al. | |
| 5,468,253 A | 11/1995 | Bezwada | |
| 5,474,529 A | 12/1995 | Arenberg | |
| 5,476,446 A | 12/1995 | Arenburg | |
| 5,538,735 A | 7/1996 | Ahn | |
| 5,545,152 A | 8/1996 | Funderburk et al. | |
| 5,563,140 A | 10/1996 | Ehrenberger et al. | |
| 5,643,207 A | 7/1997 | Rise | |
| 5,690,652 A | 11/1997 | Wurster et al. | |
| 5,707,361 A | 1/1998 | Slettenmark | |
| 5,728,396 A | 3/1998 | Peery et al. | |
| 5,836,935 A | 11/1998 | Ashton et al. | |
| 5,849,015 A | 12/1998 | Haywood et al. | |
| 5,863,927 A | 1/1999 | Smith et al. | |
| 5,865,789 A | 2/1999 | Hattler | |
| 5,895,372 A | 4/1999 | Zenner et al. | |
| 5,945,052 A | 8/1999 | Schryver et al. | |
| 5,971,953 A | 10/1999 | Bachynsky | |
| 5,980,928 A | 11/1999 | Terry | |
| 5,985,305 A | 11/1999 | Peery et al. | |
| 6,045,528 A * | 4/2000 | Arenberg et al. | 604/28 |
| 6,066,652 A | 5/2000 | Zenner et al. | |
| 6,067,474 A | 5/2000 | Schulman et al. | |
| 6,129,753 A | 10/2000 | Kuzma | |
| 6,181,969 B1 | 1/2001 | Gord | |
| 6,219,580 B1 | 4/2001 | Faltys et al. | |
| 6,309,410 B1 | 10/2001 | Kuzma et al. | |
| 6,377,849 B1 * | 4/2002 | Lenarz et al. | 604/21 |
| 6,409,698 B1 | 6/2002 | Robinson et al. | |
| 6,436,405 B1 | 8/2002 | Bakaletz et al. | |
| 6,440,102 B1 | 8/2002 | Arenberg et al. | |
| 6,450,984 B1 | 9/2002 | Lynch et al. | |
| 6,458,118 B1 | 10/2002 | Lent et al. | |
| 6,464,687 B1 | 10/2002 | Ishikawa et al. | |
| 6,568,910 B1 | 5/2003 | Parce | |
| 6,585,703 B1 | 7/2003 | Kassel et al. | |
| 6,596,752 B1 | 7/2003 | Lobl et al. | |
| 6,613,026 B1 | 9/2003 | Palasis et al. | |
| 6,627,246 B2 | 9/2003 | Mehta et al. | |
| 6,648,873 B2 * | 11/2003 | Arenberg et al. | 604/509 |
| 6,656,172 B1 | 12/2003 | Hildebrand | |
| 6,670,321 B1 | 12/2003 | Adamis | |
| 6,685,697 B1 * | 2/2004 | Arenberg et al. | 604/890.1 |
| 6,692,481 B2 | 2/2004 | Guerrero | |
| 6,718,209 B2 | 4/2004 | Williamson et al. | |
| 6,726,678 B1 | 4/2004 | Nelson et al. | |
| 6,743,204 B2 | 6/2004 | Christenson et al. | |
| 6,764,472 B1 | 7/2004 | Burke et al. | |
| 6,796,957 B2 | 9/2004 | Carpenter et al. | |
| 6,827,559 B2 | 12/2004 | Peters et al. | |
| 6,858,220 B2 | 2/2005 | Greenberg et al. | |
| 6,894,456 B2 | 5/2005 | Tsukamoto et al. | |
| 6,962,580 B2 | 11/2005 | Adams et al. | |
| 7,044,942 B2 * | 5/2006 | Jolly et al. | 604/891.1 |
| 7,060,284 B1 | 6/2006 | Kaumaya et al. | |
| 7,181,287 B2 | 2/2007 | Greenberg | |
| 7,200,504 B1 | 4/2007 | Fister | |
| 7,242,985 B1 | 7/2007 | Fridman et al. | |
| 7,272,449 B2 | 9/2007 | Dadd et al. | |
| 7,277,760 B1 | 10/2007 | Litvak et al. | |
| 7,297,130 B2 | 11/2007 | Bergheim et al. | |
| 7,347,854 B2 | 3/2008 | Shelton et al. | |
| 7,815,615 B2 | 10/2010 | Jolly | |
| 2001/0041870 A1 | 11/2001 | Gillis et al. | |
| 2002/0095133 A1 | 7/2002 | Gillis et al. | |
| 2002/0182186 A1 | 12/2002 | Loeb | |
| 2002/0183722 A1 | 12/2002 | Harper et al. | |
| 2002/0188282 A1 | 12/2002 | Greenberg | |
| 2003/0097121 A1 | 5/2003 | Jolly et al. | |
| 2003/0114830 A1 | 6/2003 | Guerrero | |
| 2003/0171738 A1 | 9/2003 | Konieczynski et al. | |
| 2003/0203890 A1 | 10/2003 | Steiner et al. | |
| 2003/0229336 A1 | 12/2003 | Jacobsen et al. | |
| 2004/0015204 A1 | 1/2004 | Whitehurst et al. | |
| 2004/0015205 A1 | 1/2004 | Whitehurst et al. | |
| 2004/0043052 A1 | 3/2004 | Hunter et al. | |
| 2004/0044389 A1 | 3/2004 | Crawford | |
| 2004/0049175 A1 | 3/2004 | Speck et al. | |
| 2004/0091995 A1 | 5/2004 | Schlom et al. | |
| 2004/0105888 A1 | 6/2004 | Pratt et al. | |
| 2004/0141925 A1 | 7/2004 | Bosch et al. | |
| 2004/0156858 A1 | 8/2004 | Franzusoff et al. | |
| 2004/0172005 A1 | 9/2004 | Arenberg et al. | |
| 2004/0209836 A1 | 10/2004 | Spencer et al. | |
| 2004/0223949 A1 | 11/2004 | Astsaturov et al. | |
| 2004/0243182 A1 | 12/2004 | Cohen et al. | |
| 2004/0267238 A1 | 12/2004 | Haarala et al. | |
| 2005/0013812 A1 | 1/2005 | Dow et al. | |
| 2005/0049578 A1 | 3/2005 | Tu et al. | |
| 2005/0085778 A1 | 4/2005 | Parks | |
| 2005/0101878 A1 | 5/2005 | Daly et al. | |
| 2005/0119636 A1 | 6/2005 | Haffner et al. | |
| 2005/0130904 A1 | 6/2005 | Schloss | |
| 2005/0130920 A1 | 6/2005 | Simard et al. | |
| 2005/0137651 A1 | 6/2005 | Litvak et al. | |
| 2005/0184004 A1 | 8/2005 | Rodgers et al. | |
| 2005/0186245 A1 * | 8/2005 | Hunter et al. | 424/423 |
| 2005/0233964 A1 | 10/2005 | Kaumaya et al. | |
| 2005/0238506 A1 | 10/2005 | Mescher et al. | |
| 2005/0245906 A1 | 11/2005 | Makower et al. | |
| 2005/0256560 A1 | 11/2005 | Lenarz | |
| 2005/0267422 A1 * | 12/2005 | Kriesel | 604/288.01 |
| 2006/0009805 A1 | 1/2006 | Jensen et al. | |
| 2006/0030837 A1 | 2/2006 | McKenna et al. | |
| 2006/0041182 A1 | 2/2006 | Forbes et al. | |
| 2006/0047270 A1 | 3/2006 | Shelton | |
| 2006/0063802 A1 | 3/2006 | Guitton et al. | |
| 2006/0100672 A1 | 5/2006 | Litvak | |
| 2006/0106446 A1 | 5/2006 | Fridman et al. | |
| 2006/0177495 A1 | 8/2006 | Allen et al. | |
| 2006/0205789 A1 | 9/2006 | Lobl et al. | |
| 2006/0264897 A1 * | 11/2006 | Lobl et al. | 604/506 |
| 2007/0015727 A1 | 1/2007 | Puel et al. | |
| 2007/0088335 A1 * | 4/2007 | Jolly | 604/891.1 |
| 2007/0123938 A1 | 5/2007 | Haller et al. | |
| 2007/0260292 A1 | 11/2007 | Faltys et al. | |
| 2007/0287984 A1 | 12/2007 | Lobl et al. | |
| 2008/0009836 A1 | 1/2008 | Fiering et al. | |
| 2008/0033520 A1 * | 2/2008 | Jolly | 607/137 |
| 2008/0065002 A1 | 3/2008 | Lobl et al. | |
| 2008/0145439 A1 | 6/2008 | Lobl et al. | |
| 2008/0152694 A1 | 6/2008 | Lobl et al. | |

FOREIGN PATENT DOCUMENTS

| | | |
|---|---|---|
| JP | S5482497 | 6/1979 |
| WO | 9504571 | 2/1995 |
| WO | 9727840 | 8/1997 |
| WO | 9917819 | 4/1999 |
| WO | 0004854 | 2/2000 |
| WO | 0033775 | 6/2000 |
| WO | 03034960 | 5/2003 |
| WO | 03072193 | 9/2003 |
| WO | WO 03/099351 | 12/2003 |
| WO | 2004022069 | 3/2004 |
| WO | 2006053101 | 5/2006 |

OTHER PUBLICATIONS

Hirbec, et al., "Gacyclidine: A New Neuroprotective Agent Acting at the N-Methyl-D-Aspartate Receptor", CNS Drug Reviews, vol. 7, No. 2, pp. 172-198, 2001.

International Search Report from PCT/US07/09753 dated Dec. 26, 2007.

International Search Report and Written Opinion from PCT/US06/02403 dated Dec. 4, 2007.

Lautermann, J., "Glautathione-Dependent Antioxidant Systems in the Mammalian Inner Ear: Effects of Aging, Ototoxic Drugs and Noise", Hear Res., Dec. 1997, 114 (1-2) p. 75, Abstract.

U.S. Appl. No. 11/780,853, filed Jul. 20, 2007.

U.S. Appl. No. 11/831,230, filed Jul. 31, 2007.

Konishi, T., et al. (1973), "Effect of Potassium Deficiency on Cochlear Potentials and Cation Contents of the Endolymph", Acta Otolaryng 76:410-8.

Feng, B., et al., (2004), "Structure-Activity Analysis of a Novel NR2C/NR2D-Preferring NMDA Receptor Antagonist: 1-(phenanthrene-2-carbonyl) piperazine-2,3-dicarboxylic acid", Br. J. Pharmacol. 141:508-516.

Geneste P., et al. (1979) "Détermination conformationnelle de dérivés de la phenycyclidine en vue d'une corrélation structure-activité", Eur. J. Med. Chem. 14:301-308.

Hansen, R.E., et al., (1988) "Determination of the Regime of Rapid Reacting Systems in Stopped- and Steady-flow Investigations by the Velocity Probe Method", J. Phys. Chem. 92:2189-2196.

Lu Y, et al. (2004) "Micro and Nano-Fabrication of Biodegradable Polymers for Drug Delivery", Adv. Drug Deliv. Rev. 56:1621-1633.

Morris A.W., et al. (1989), "Cochlear Dialysis for Meniere's Disease", An Update. Am J. Otol. 10:148-9.

Muly S.M., et al. (2004) "Noise Trauma Alters D-[3H]aspartate Release and AMPA Binding in Chinchilla Conchlear Nucleus", J. Neurosci. Res. 75:585-596.

Orive G., et al., (2005) "Micro and Nano Drug Delivery Systems in Cancer Therapy", Cancer Therapy 3:131-138.

Prakobvaitayakit M., et al. (2003) "Optimization of polylactic-co-glycolic Acid Nanoparticles Containing Itraconizole Using 23 Factorial Design", AAPS PharmaSciTech 4(4):Article 71 (http://www.aapspharmascitech.org).

Takizawa S., et al. (1995), "A Selective N-type Calcium Channel Antagonist Reduces Extracellular Glutamate Release and Infarct Volume In Focal Cerebral Ischemia", J. Cerebral Blood Flow Metab. 15:611-8.

Mizukoshi, et al., "Drug Delivery to the Cochlea Using Poly Lactic/glycolic Acid Nanoparticles", Abstracts of the Twenty-Ninth Annual Midwinter Research Meeting, Feb. 5-9, 2006, ARO Abstracts, vol. 29, 2006, 5 pages.

Sun, et al., "Neurotrophin-3 Gene Transfection of Cochlear Cells with hydroxyapatite Nanoparticle Vector", Abstracts of the Twenty-Ninth Annual Midwinter Research Meeting, Feb. 5-9, 2006, ARO Abstracts, vol. 29, 2006, 5 pages.

Pedrini, et al., "Evaluation of Thrombogenicity of Fluoropassivated Polyester Patches Following Carotid Endarterectomy", Nov. 2001 Ann. Vasc. Surg. 15(6):679-83.

Kim, et al., "An Experimental Study on Thrombogenicity of Various Metallic Microcoils with or without Thrombogenic Coatings" Jul. 1998, Invest. Radiol. 33(7):407-410.

Hong, et al., "Material-Specific Thrombin Generation Following Contact Between Metal Surfaces and Whole Blood", Apr. 2005, Biomaterials 26(12):1397-403.

Salt A.N., et al., (1998) "Longitudinal Endolymph Movements Induced by Perilymphatic Injections", Hearing Research 123:137-147.

Feijen R.A., et al., (Mar. 1, 2002) "Change of Guinea Pig Inner Ear Pressure by Square Wave Middle Ear Cavity Pressure Variation", Acta Otolaryngologica, 122:No. 2:138-45.

Sennaroglu L., et al., (Sep. 2001) "Relationship of Vestibular Aqueduct and Inner Ear Pressure in Meniere's Disease and the Normal Population", Laryngoscope 111:1625-1630.

Salt AN, et al., (2003), "Contamination of Perilymph Sampled from the Basal Cochlear Turn with Cerebrospinal Fluid", Hearing Research 182:24-33.

U.S. Appl. No. 61/022,224, filed Jan. 18, 2008.

Rodrigues CM, et al., (2003), "Tauroursodeoxycholic Acid Reduces Apoptosis and Protects Against Neurological Injury After Acute Hemorrhagic Stroke in Rats", Proc Natl Acad Sci USA 100:6087-6092.

U.S. Appl. No. 60/665,171, filed Mar. 24, 2005.
U.S. Appl. No. 11/008,869, filed Dec. 9, 2004.
U.S. Appl. No. 11/016,604, filed Dec. 16, 2004.
U.S. Appl. No. 11/089,171, filed Mar. 24, 2005.
U.S. Appl. No. 11/122,648, filed May 5, 2005.
U.S. Appl. No. 11/139,296, filed May 26, 2005.
U.S. Appl. No. 11/178,054, filed Jul. 8, 2005.
U.S. Appl. No. 11/226,777, filed Sep. 13, 2005.
U.S. Appl. No. 11/261,432, filed Oct. 28, 2005.
U.S. Appl. No. 11/262,055, filed Oct. 28, 2005.
U.S. Appl. No. 11/386,198, filed Mar. 21, 2006.

Gaviria, et al., "Neuroprotective Effects of a Novel NMDA Antagonist, Gacycylidine, after Experimental Contusive Spinal Cord Injury in Adult Rats", Brian Research, vol. 874, Iss. 2, Aug. 25, 2000, pp. 200-209.

International Search Report and Written Opinion for PCT/US07/13686 dated Jul. 23, 2008.

International Search Report and Written Opinion for PCT/US07/19385 dated Jul. 28, 2008.

András Hermann, et al., "Interference of S-Nitrosoglutathione with the Binding of Ligands to Ionotropic Glutamate Receptors in Pig Cerebral Cortical Synaptic Membranes," *Neurochemical* Research, vol. 25, No. 8, 2000, pp. 1119-1124.

C.P. Taylor, "Mechanisms of Action of Gabapentin", Rev Neurol (Paris), 1997; 153 Suppl. 1:S39-45.

Piotr Popik, et al., "The Putative Anti-Addictive Drug Ibogaine is a Competitive Inhibitor of [$^3$H]MK-801 Binding to the NMDA Receptor Complex", Psychopharmacology (1994) 114: 672-674.

Mark J. Ginski, et al., "Sensitive and Rapid Behavioral Differentiation of N-methyl-D-aspartate Receptor Antagonists", Psychopharmacology (1994) 114:573-582.

Karin Agerman, et al., "Neurotrophins, NMDA Receptors, and Nitric Oxide in Development and Protection of the Auditory System", Annals New York Academy of Sciences, Nov. 28, 1999, 884:131-142.

Anthony S. Basile, et al., "*N*-Methyl-D-aspartate Antagonists Limit Aminoglycoside Antibiotic-Induced Hearing Loss", Nature Medicine, vol. 2, No. 12, Dec. 1996, pp. 1338-1343.

Zhiqiang Chen, et al., "Acute Treatment of Noise Trauma with Local Caroverine Application in the Guinea Pig", Acta Otolaryngol, Oct. 2003; 123(8):905-909.

Zhiqiang Chen, et al., "Protection of Auditory Function Against Noise Trauma with Local Caroverine Administration in Guinea Pigs", Hearing Research 197 (1-2), 2004, pp. 131-136.

E. Costa, "From $GABA_A$ Receptor Diversity Emerges a Unified Vision of GABAergic Inhibition", Annu. Rev. Pharmacol. Toxicol. 1998, 38:321-50.

Maoli Duan, et al., "Complementary Roles of Neurotrophin 3 and a *N*-methyl-D-aspartate Antagonist in the Protection of noise and Aminoglycoside-induced Ototoxicity", PNAS, Jun. 20, 2000, vol. 97, No. 13, pp. 7597-7602.

Sophie Feldblum, et al., "Efficacy of a New Neuroprotective Agent, Gacyclidine, in a Model of Rat Spinal Cord Injury", Journal of Neurotrauma, vol. 17, No. 11, 2000, pp. 1079-1093.

Frauke Fischer, et al., "List of Drugs in Development for Neurodegenerative Diseases", Neurodegenerative Dis 2004; 1:50-70.

Ruggero Galici, et al., "Tolerance to and Dependence on Alprazolam are Due to Changes in $GABA_A$ Receptor Function and are Independent of Exposure to Experimental Set-up", Restorative Neurology and Neuroscience 12 (1998); pp. 233-237.

Michael J. Gallagher, et al., "Interactions Between Ifenprodil and the NR2B Subunit of the *N*-Methyl-D-aspartate Receptor", The Journal of Biological Chemistry, vol. 271, No. 16, Issue of Apr. 19, 1996, pp. 9603-9611.

Matthieu J. Guitton, et al., "New Pharmacological Strategies to Restore Hearing and treat Tinnitus", Acta Otolaryngol, 2004; 124: 411-415.

Greta Ann Herin, et al., "The Neuroprotective Agent Ebselen Modifies NMDA Receptor Function via the Redox Modulatory Site", Journal fo neurochemistry, 2001, 78, 1307-1314.

B.K. Kohl, et al., "The NMDA Receptor Complex: A Promising Target for Novel Antiepileptic Strategies", Current Medicinal Chemistry, Sep. 2001, 8, 1275-1289.

Richard D. Kopke, et al., "Enhancing Intrinsic Cochlear Stress Defenses to Reduce Noise-Induced Hearing Loss", The Laryngoscope 112: Sep. 2002, pp. 1515-1532.

David B. Moody, "Animal Models of Tinnitus", Tinnitus: Theory and Management, Chapter 7, pp. 80-95 (2004).

Alan L. Mueller, et al., "NPS 1506, A Novel NMDA Receptor Antagonist and Neuroprotectant, Review of Preclinical and Clinical Studies", Annals New York Academy of Sciences, 1999; 890:450-457.

M. Nankai, et al., "NMDA Receptor Subtype Selectivity: Eliprodil, Polyamine Spider Toxins, Dextromethorphan, and Desipramine Selectively Block NMDA-Evoked Striatal Acetylcholine but Not Spermidine Release", Journal of Neurochemistry, May 1995; 64(5): pp. 2043-2048.

Nagendra S. Ningaraj, et al., "S-Methyl-N, N-Diethylthiocarbamate Sulfoxide Elicits Neuroprotective Effect against N-Methyl-*D*-Aspartate Receptor-Mediated Neurotoxicity", Journal of Biomedical Science 2001; 8:104-113.

Dominik Oliver, et al., "Memantine Inhibits Efferent Cholinergic Transmission in the Cochlea by Blocking Nicotinic Acetylcholine Receptors of Outer Hair Cells", Molecular Pharmacology, vol. 60, No. 1, Jul. 2001; 60(1):183-189.

Wojciech Danysz, et al., "Glycine and N-Methyl-D-Aspartate Receptors: Physiological Significance and Possible Therapeutic Applications", Pharmacological Reviews, vol. 50, No. 4, pp. 597-664 (1998).

Gene C. Palmer, "Neuroprotection by NMDA Receptor Antagonists in a Variety of Neuropathologies", Current Drug Targets, Sep. 2001, 2(3):241-71.

Rémy Pujol, et al., "Excitotoxicity, Synaptic Repair, and Functional Recovery in the Mammalian Cochlea: A Review of Recent Findings", Annals of the New York Academy of Sciences, 1999, 884: 249-254.

Stephen M. Stahl, "Anticonvulsants and the Relief of Chronic Pain: Pregabalin and Gabapentin as $a_2\delta$ Ligands at Voltage-Gated Calcium Channels", J. Clin. Psychiatry 65:5, May 2004, pp. 596-597.

Masahiro Sugimoto, et al., Local Anaesthetics Have Different Mechanisms and Sites of Action at the Recombinant N-methyl-D-aspartate (NMDA) Receptors), British Journal of Pharmacology (2003) 138, 876-882.

Li-Ming Zhou, et al., "Synthetic Analogues of Conantokin-G: NMDA Antagonists Acting Through a Novel Polyamine-Coupled Site", Jounral of Neurochemistry, Feb. 1996, 66(2): 620-8.

David R. Lynch, et al., "Pharmacological Characterization of Interactions of RO 25-6981 with the NR2B ($\epsilon$2) Subunit", European Journal of Pharmacology 416 (2001):185-195.

David R. Lynch, et al., "Inhibition of N-Methyl-D-Aspartate Receptors by Haloperidol: Developmental and Pharmacological Characterization in Native and Recombinant Receptors", The Journal of Pharmacology and Experimental Therapeutics, vol. 279, No. 1, Oct. 1996:154-61.

Matthieu J. Guitton, et al., "New Pharmacological Strategies to Restore Hearing and Treat Tinnitus", Acta Otolaryngol 2004; 124:411-415.

Barbara A. Goldstein, et al., "Tinnitus Outcome Profile and Tinnitus Control", International Tinnitus Journal, vol. 9, No. 1, 2003: 26-31.

Doris-Maria Denk, et al., "Caroverine in Tinnitus Treatment", Acta Otolaryngol (Stockh) 1997; 117:825-830.

M.B. Hesselink, et al., "Modifications of the Behavioral Profile of Non-Competitive NMDA Receptor Antagonists, memantine, amantadine and (+)MK-801 after Chronic Administration", Behavioural Pharmacology 1999; 10:85-98.

Wojciech Danysz, et al., "Neuroprotective Potential of Ionotropic glutamate Receptor Antagonists", Neurotoxicity Research, 2002, vol. 4(2), pp. 119-126.

T. Oma Hester, et al., "Cyclandelate in the Management of Tinnitus: A Randomized, Placebo-Controlled Study", Otolaryngol Head neck Surg., Mar. 1998, 118(3, Pt. 1): 329-332.

Jan H. Hulshof, et al., "The Value of Tocainide in the Treatment of Tinnitus, A Double-Blind Controlled Study", Arch Otorhinolaryngol (1985) 241:279-283.

Th. Lenarz, "Treatment of Tinnitus with Lidocaine and Tocainide", Scand. Audiol. Suppl., 1986: 26:49-51.

Leif Nordang, et al., "Glutamate is the Afferent Neurotransmitter in the Human Cochlea", Acta Otolaryngol 2000; 120:359-362.

Elmar Oestreicher, et al., "Memantine Suppresses the Glutamatergic Neurotransmission of Mammalian Inner Hair Cells", ORL J. Otorhinolaryngol Relat. Spec., Jan.-Feb. 1998; 60(1):18-21.

Elmar Oestreicher, et al., "New Approaches for Inner Ear Therapy with Glutamate Antagonists", Acta Otolaryngol, Mar. 1999; 119(2):174-178.

Elmar Oestreicher, et al., "Different Action of Memantine and Caroverine on Glutamatergic Transmission in the Mammalian Cochlea", Adv. Otorhinolaryngol, 2002; 59:18-25.

E. Perucca, et al., A Controlled Study of the Suppression of Tinnitus by Lidocaine Infusion: (Relationship of Therapeutic Effect with Serum Lidocaine Levels); The Journal of Laryngology and Otology, Jul. 1985, vol. 99, pp. 657-661.

Michael D. Seidman, et al., "Pharmacologic Manipulation of the Labyrinth with Novel and Traditional Agents Delivered to the Inner Ear", ENT-Ear, Nose & Throat Journal, Apr. 2003; 82(4): 276-280, 282-283, 287-288.

Wojciech Danysz, et al., "Glutamate Antagonists Have Different Effects on Spontaneous Locomotor Activity in Rats", Pharmacology Biochemistry and Behavior, 1994, vol. 48, No. 1, pp. 111-118.

Chrysanthy Ikonomidou, et al., "Why did NMDA Receptor Antagonists Fail Clinical Trials for Stroke and Traumatic Brain Injury?", The Lancet neurology, vol. 1(6), Oct. 2002: 383-386.

T. Lenarz, et al., "Tinnitus Therapy with Liodcaine and Tocainide", Laryngol Rhinol. Otol (Stuttg.); Dec. 1985, 64(12):604-608 (with English Abstract).

K. Ogita, et al., "Nitric Oxide-Independent Inhibition by Sodium Nitroprusside of the Native *N*-methyl-D-aspartate Recognition Domain in a Manner Different from that by Potassium Ferrocyanide", Neurochem. Int. 33 (1998):1-9.

Steven L. Peterson, et al., "Differential Neuroprotective Effects of the NMDA Receptor-Associated Glycine Site Partial Agonists 1-Aminocyclopropanecarboxylic Acid (ACPC) and D-Cycloserine in Lithium-Pilocarpine Status Epilepticus", NeuroToxicology 25 (2004):835-847.

Margaret A. Petty, et al., "ACEA 1021: Flip or Flop?", CNS Drive Reviews, vol. 10, No. 4, pp. 337-348 (2004).

Jacob B. Schwarz, et al., "Novel Cyclopropyl β-Amino Acid Analogues of Pregabalin and gabapentin that Target the $a_2\delta$ Protein", J. Med. Chem. 2005, 48, pp. 3026-3035.

Paolo Calabresi, et al., "Ionotropic Glutamate Receptors: Still a Target for Neuroprotection in Brain Ischemia? Insights from In Vitro Studies", Neurobiology of Disease, 12 (2003): pp. 82-88.

Stanislaw J. Czuczwar, et al., "The New Generation of GABA Enhancers, Potential in the Treatment of Epilepsy", CNS Drugs, 2001; 15(5):339-350.

David J. Hewitt, et al., "The Use of NMDA-Receptor Antagonists in the Treatment of Chronic Pain", The Clinical Journal of Pain, Jun. 2000; 16(2 Suppl.):S73-79.

Sveta Mayer, et al., "Acamprosate, MK-801, and Ifenprodil Inhibit Neurotoxicity and Calcium Entry Induced by Ethanol Withdrawal in Organotypic Slice Cultures from Neonatal Rat Hippocampus", Alcohol Clin. Exp. Res., Oct. 2002; 26(10):1468-78.

Zhang-Lin Zhou, et al., "4-Hydroxy-1-[2-(4-hydroxyphenoxy)ethyl]-4-(4-methylbenzyl)piperidine: A Novel, Potent, and Selective NR1/2B NMDA Receptor Antagonist", J. Med. Chem. 1999, 42, 2993-3000.

Richard K. Gordon, et al., "The NMDA Receptor Ion Channel: a Site for Binding of Huperzine A", Journal of Applied Toxicology, 2001;21:S47-S51.

C.G. Parsons, et al., "Comparison of the Potency, Kinetics and Voltage-Dependency of a Series of UnCompetitive NMDA Receptor Antagonists In Vitro with Anticonvulsive and Motor Impairment Activity In Vitro", Neuropharmacology, 1995; vol. 34, No. 10, pp. 1239-1258.

Naveen K. Dakappagari, et al., "A Chimeric Multi-Human Epidermal Growth Factor Receptor-2 B Cell Epitope Peptide Vaccine Mediates Superior Antitumor Responses", *The Journal of Immunology*, 170:4242-4253 (2003).

Pravin T.P. Kaumaya, et al., "Design and Immunological Properties of Topographic Immunogenic Determinants of a Protein Antigen (LDH-$C^4$) as Vaccines", *The Journal of Biological Chemistry*, vol. 267, No. 9, Mar. 25, 1992, pp. 6338-6346.

Susan Kobs-Conrad, et al., Engineered Topographic Determinants with αβ, βαβ, and βαβα Topologies Show High Affinity Binding to Native Protein Antigen (Lactate Dehydrogenase-$C_4$), *The Journal of Biological Chemistry*, vol. 268, No. 34, Dec. 5, 1993, pp. 25285-25295.

International Search Report and Written Opinion for PCT/US07/16414 dated Aug. 12, 2008.
International Search Report and Written Opinion for PCT/US07/17109 dated Aug. 22, 2008.
Search Report in EP 07795973.2 dated Mar. 8, 2011.
Notice of Reasons for Rejection in JP 2007/552359 dated Mar. 30, 2011.
Gaviria, M., et al., "Neuroprotective Effects of a Novel NMDA Antagonist, Gacyclidine, After Experimental Contusive Spinal Cord Injury in Adult Rats", Brian Research, vol. 874, Iss. 2, Aug. 25, 2000, p. 200-209.

Supplementary European Search Report for EP07755859 dated Jun. 9, 2010.
U.S. Appl. No. 11/374,505, filed Mar. 13, 2006.
U.S. Appl. No. 10/281,066, filed Oct. 24, 2002.
U.S. Appl. No. 60/336,452, filed Oct. 24, 2001.
U.S. Appl. No. 60/394,427, filed Jul. 8, 2002.
U.S. Appl. No. 60/394,602, filed Jul. 9, 2002.
U.S. Appl. No. 60/417,704, filed Oct. 10, 2002.
U.S. Appl. No. 60/780,667, filed Mar. 9, 2006.

* cited by examiner

APPARATUS AND METHOD FOR DELIVERY OF THERAPEUTIC AND OTHER TYPES OF AGENTS

BACKGROUND OF THE INVENTION

It is known that drugs work most efficiently in the human body if they are delivered locally, e.g., to a specific tissue to be treated. When a drug is delivered systemically, tissues other than those being treated may be exposed to large quantities of that drug. This exposure presents a much greater chance for side effects. Targeting drug delivery to specific tissue often presents challenges, particularly if the targeted tissues are deep inside the body. In many cases, one or more doses of a drug or other agent can only be delivered to certain tissues with a specialized injection device.

One group of tissues which can be difficult to reach include the cochlea and other specific sub-cochlear locations in the inner ear. Therapeutic agents can be delivered to either the middle ear or the inner ear for the treatment of various diseases and conditions associated with inner ear tissue. Areas of the inner ear tissue structures where treatment can be beneficial include portions of the osseous labyrinth, such as the cochlea. However, the delivery of therapeutic agents to the inner ear in a controlled and effective manner is difficult due to the size and structure of the inner ear. The same is true of the tissue materials which separate the middle ear from the inner ear (e.g. the round window membrane). The inner ear tissues are of such sizes and locations that they are only readily accessible through invasive microsurgical procedures.

Access to the osseous labyrinth in the inner ear, including the cochlea, is typically achieved through a variety of structures of the middle-inner ear interface including, but not limited to, the round window membrane or the temporal bone. As known, the middle ear region includes the air-containing tissue zone between the tympanic membrane (e.g. the ear drum) and the inner ear. Currently, a variety of methods exist for delivering therapeutic agents to the middle ear and inner ear for treating inner ear diseases and conditions. These methods include drug injection through the tympanic membrane and surgically implanting drug loaded sponges and other drug releasing materials. Although conventional methods may ultimately result in the delivery of a therapeutic agent into the inner ear (e.g., by perfusion through the round window membrane), that delivery is generally not well controlled and the amount of the therapeutic agent that arrives within the inner ear is not precisely known.

Numerous other anatomical regions can be difficult to access without invasive surgical procedures. For example, it is often beneficial to treat cancer, allergy-related disorders and various auto-immune diseases by direct injection of drugs into a lymph node (e.g., treating allergies with immune suppressants or drugs that change the immune response from IgE to IgG). Many tumors can also be treated effectively with targeted delivery of various compounds. In many cases, however, a targeted lymph node, tumor or other anatomical region can only be located using specialized and time-consuming techniques such as radiological procedures, affinity techniques in which antibodies target cell surface antigens, or enzyme targeted pro-drug techniques. Supplying small amounts of a drug over an extended period to not-easily-accessible regions can pose practical problems. Each treatment may require a complicated, invasive and expensive medical procedure. Repeated surgical interventions over time are in most cases undesirable to the medical community and/or patients.

There are numerous other circumstances in which it may be desirable to deliver drugs or other agents in a tissue-specific manner on an intermittent or continuous basis. Examples include drug delivery to the brain for treatment of chronic pain, migraines, conditions of the auditory cortex, conditions of the inferior colliculus, and various neurological disorders.

In situations such as those described above, as well as in numerous other scenarios, conventional methods and systems do not deliver agents to a desired location in a controlled and efficient manner. As a result, the amount and frequency of agents introduced into an intended anatomical region cannot be effectively controlled.

SUMMARY OF THE INVENTION

This Summary is provided to introduce a selection of concepts in a simplified form that are further described below in the Detailed Description. This Summary is not intended to identify key or essential features of the claimed subject matter, nor is it intended to be used as an aid in determining the scope of the claimed subject matter.

Some embodiments of the invention include implantable drug delivery systems which can be used for targeted delivery of drugs to specific tissues. Using such systems, small volumes of drugs can be delivered to target tissues, either intermittently or continuously, on a short-term or a long-term (e.g., several months or years) basis. In some embodiments, an implanted osmotic pump is in fluid communication with a drug/filter capsule, a catheter, and a needle or other implemented terminal component. The terminal component (which may be a needle, cochlear catheter, cochlear implant electrode, etc.) delivers drug(s) to a target tissue. In at least some other embodiments, the implanted drug-delivery system includes a subcutaneous (SC) port, catheter, and needle (or other terminal component) for ultimate delivery of drug to a target tissue. An external pump (i.e., outside of the patent's body) is connected to the SC port. The external pump can in some implementations supply a liquid formulated drug to the port.

Both solid and liquid drug formulations can be used, however. In embodiments using solid drugs, a separate drug vehicle can be used to dissolve a portion of a solid drug contained in an SC port reservoir or a drug-holding capsule. The vehicle (e.g., saline, Ringer's solution, artificial perilymph, etc.) is then delivered to the target tissue via an implanted catheter. In some cases, the vehicle is supplied from an external pump. In still other cases, the vehicle is supplied from an implanted osmotic pump.

Embodiments of the invention include and/or facilitate treatments that include, but are not limited to, delivery of drugs to the inner ear for treatment of hearing-related and other ailments such as tinnitus, infections of the inner ear, inflammatory diseases, inner ear cancer, acoustic neuroma, acoustic trauma, Ménière's Disease, etc.; delivery of drugs to the brain for treatment of chronic pain, mental illnesses and other diseases of the central nervous system; and delivery of drugs to tumors, diseased tissue and lymph nodes for treatment of cancer, allergies, autoimmune diseases and other maladies.

BRIEF DESCRIPTION OF THE DRAWINGS

The foregoing summary of the invention, as well as the following detailed description of preferred embodiments, are better understood when read in conjunction with the accompanying drawings, which are included by way of example, and not by way of limitation with regard to the claimed invention.

DETAILED DESCRIPTION

Figure 1:
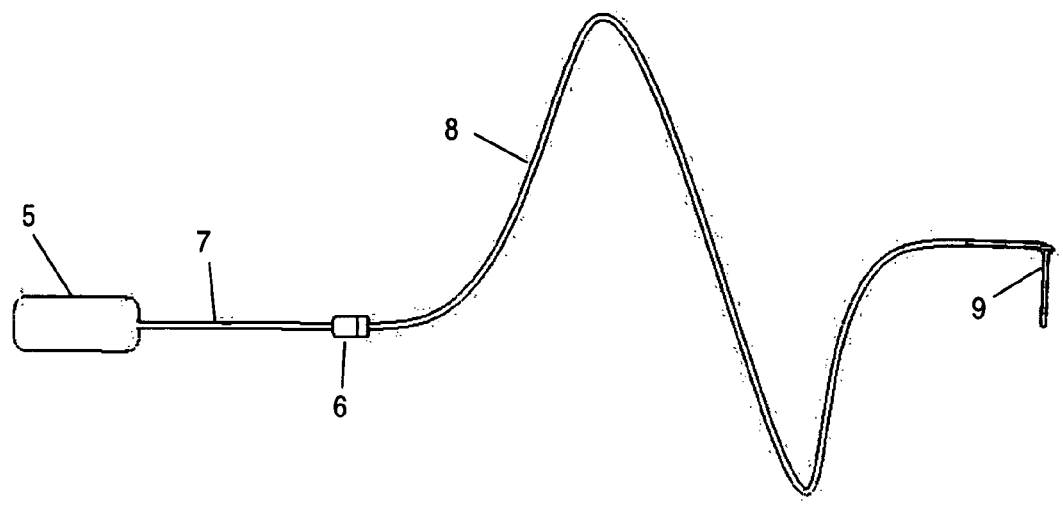
FIG. 1 is a drawing of an implantable drug delivery system, according to at least some embodiments, that includes an osmotic pump and solid drug/filter housing.

At least some embodiments of the invention include systems that permit targeted delivery of drugs to a specific anatomical region, intermittently or continuously, and on a short-term or a long-term basis. The following description provides numerous examples of devices and methods according to certain of these embodiments. However, the invention is not limited to the specific devices described (or to the specifically-described uses for those devices). Various embodiments are described as usable for delivery of drugs. As used herein, including the claims, "drug" is not limited to a therapeutic compound. Instead, "drug" includes diagnostic and other types of agents. The following description also provides examples of some of the tissues to which drugs may be delivered to advantage, as well as examples of diseases and other conditions which can be treated. However, the invention is not limited to use for delivery of drugs to the specifically identified tissues or for treatment of a specifically-identified disease or condition.

Drug-delivery systems according to at least some embodiments include combinations of various implantable components. These components include osmotic pumps, subcutaneous (SC) ports, catheters and terminal components. As used herein, a terminal component refers to an element with which a catheter is in fluid communication, and which delivers a drug or other agent to (or withdraws fluid from) a targeted tissue. In some embodiments, a terminal component is a straight needle, bone needle or other type of needle. In other embodiments, a terminal component may be a cochlear implant electrode. In still other embodiments, the terminal component may simply be the bare open end of the catheter. Other types of terminal components are also within the scope of the invention.

In some cases, an osmotic pump (and/or an SC port) and other system components are small enough to permit subcutaneous implantation on the side of a patient's head, and can be used for delivering drugs to the middle ear, inner ear or brain. These components can also be implanted elsewhere on a patient's body, however. In some embodiments, an SC port contains a drug within an internal reservoir or cavity. An external pumping system and infusion set is connected to the SC port. A catheter and terminal component are in fluid communication with the SC port, and are also implanted. Fluid is delivered to the SC port from the external pumping system, which fluid then transports the drug from the SC port cavity to the targeted tissue. These and other embodiments can be used for delivery of drugs to any specific tissue (e.g., middle or inner ear, lymph node, cancer tumor, arthritic joint, brain or spinal column, diseased organ, etc.). This permits various types of therapeutic applications. For example, certain drugs can be applied to generate a potent immunological response, potentially providing an immunotherapy approach to treating autoimmune diseases and for generating a vaccine-like response. Drugs can also be delivered to nerves, the spinal column, the cerebro-spinal fluid and related tissues for the treatment of chronic pain.

Embodiments of the invention can be used to deliver drugs that are in solid or in liquid formulations. Frequently, a solid drug has the advantage of maintaining its stability for longer periods of time. Solid drugs also have a high drug to volume ratio and low surface area. If solid drug is used, the solid can be eroded with a liquid from an implanted or external reservoir containing a fluid such as saline, Ringer's solution or artificial perilymph in order to dissolve the drug into the liquid, which liquid can then be delivered to the target tissue.

FIG. 1 is a drawing of a drug delivery system according to at least some embodiments. The system of FIG. 1 includes an implantable osmotic pump 5 and a drug/filter housing 6. As explained below, housing 6 includes an internal cavity, an inlet and an outlet. A lumen of first catheter 7 connects an outlet of osmotic pump 5 and an inlet of drug/filter housing 6. As used herein, a "catheter" (or "cannula") is a tube or other slender body having one or more internal lumens through which a fluid may flow. A lumen of second catheter 8 connects an outlet of drug/filter housing 6 to a bone needle 9. Bone needle 9 is configured for insertion into the cochlea through a hole drilled in the bone. Bone needle 9 is sufficiently long (for example 10 to 30 mm) to allow adequate penetration through the bone, and can be bent to allow complete implantation below the skin for long term implantation. Bone needle 9 may have an insertion stop formed from one or more biocompatible porous materials such as titanium. The porous material may be coated with a bone growth factor such as OP-1. After surgical implantation of the bone needle, the insertion stop becomes fused to (or otherwise integrated into) the bone to form a permanent connection. As can be appreciated, a fluid path is formed by pump 5, the lumen of catheter 7, the internal cavity of housing 6, the lumen of catheter 8, and bone needle 9. Other types of terminal components could be used instead of bone needle 9. For example, a system similar to that shown in FIG. 1 could alternately employ a straight needle or cochlear implant as a terminal component.

Osmotic pump 5 is of a type known in the art. Such pumps (e.g., pumps sold under the trade names DUROS® and CHRONOGESIC® by Durect Corp. of Cupertino Calif.) are known for use in other applications, and are described in, e.g., U.S. Pat. No. 4,034,756 (incorporated by reference herein). In general, an implanted osmotic pump incorporates osmotic pressure differences to drive a drug at a predefined flow rate related to the aqueous permeability of a membrane in the pump. This mechanism typically uses an osmopolymer, salt, or other material with high osmolality to imbibe liquid from the surrounding tissue environment and expand a compartment volume. This volume increase moves a piston or compresses a flexible reservoir, resulting in expulsion of a liquid from the pump. The piston (or a moveable seal) separates the osmopolymer from a reservoir containing the liquid. The pump housing may consist of a semi-permeable body which allows water or appropriate liquid to reach the osmopolymer. The rate of delivery of the pump is determined by the permeability of the pump's outer membrane.

Conventional osmotic pumps hold a liquid formulated drug in the liquid reservoir. Osmotic pump 5 in FIG. 1 instead contains a drug vehicle (such as saline, Ringer's solution or artificial perilymph). The vehicle is expelled from pump 5 for mixing with a solid drug inside of drug/filter housing 6. In other embodiments, pump 5 may expel a liquid that contains a drug, but which is also used as a vehicle to carry an additional drug from drug/filter housing 6.

Osmotic mini-pumps can deliver small amounts of liquid continuously for long periods of time. However, it can be difficult to refill an internal reservoir of a conventional osmotic pump. Accordingly, the embodiment of FIG. 1 includes a fitting (not shown in FIG. 1) that allows convenient removal and replacement of osmotic pump 5 in a brief surgical procedure. Controlling the flow rate of an osmotic pump can also be difficult. Variations on the embodiment of FIG. 1 include a controllable valve connected to the pump which isolates the semi-permeable membrane (within the pump) from low osmolality environmental fluids. This prevents entry of the fluid into the pump compartment to drive the fluid delivery piston. The control valve may be a piezoelectric element which deforms when an electrical field is applied across it. Such a valve may be connected and controlled by an internal electronics package or by an internal control module which receives signals through RF transmission (e.g., from an external signal system worn by the patient outside the body). In still other embodiments, a small magnetically activated switch is built into the electronics for the valve. The valve is opened or closed by placing a magnet of sufficient strength over the portion of the patient's body where the control electronics have been implanted. Similar magnetically activated switches are found in implanted devices such as pacemakers and implanted cardiac defibrillators. Even when such control valves are employed, however, an osmotic pump may not function in an instant-on/instant-off manner. For example, there may be a delay between the time a control valve is closed and the time that the pump delivery tapers off; during this delay the pump is reaching osmotic equilibrium. In yet other embodiments, this can be addressed by placing a control valve or a diverter valve on the pump outlet catheter 7. In still other embodiments, a pressure release valve could be included to drain away osmotic pressure in emergency situations requiring immediate pump shutdown.

Figure 2:
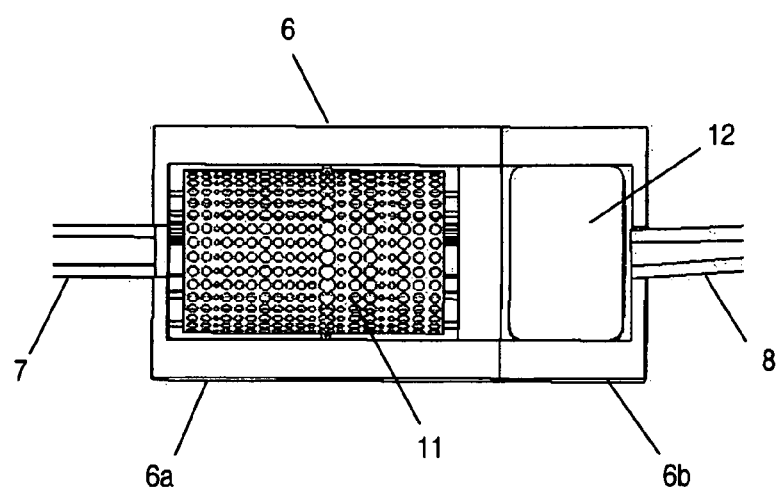
FIG. 2 is a cross-sectional view of the solid drug/filter housing shown in FIG. 1.

FIG. 2 is a cross-sectional view of drug/filter housing 6 from FIG. 1. Housing 6 serves as a capsule to hold one or more solid drugs and an antibacterial filter. Housing 6 is formed from titanium or other material which is both biocompatible and compatible with drugs to be dispensed. A proximal (or "upstream") end of housing 6 holds a porous cage 11 which may be permanently attached to the housing, or which may be removable. Cage 11, which is also formed from titanium or other bio- and drug-compatible material(s), holds a solid drug. That drug may be monolithic, in the form of a powder, in the form of pellets, or in some other solid configuration. Multiple holes on cage 11 allow fluid from pump 5 to mix with and carry away a portion of that solid drug in dissolved form. A distal (or "downstream") end of holder 6 contains a three-dimensional antibacterial filter 12. As used herein, an "antibacterial filter" is a filter having a pore size that is small enough to allow a drug-carrying fluid to pass, but which obstructs passage of bacteria or other undesirable elements. Housing 6 is a two piece assembly (pieces 6a and 6b), thereby allowing housing 6 to be taken apart and reassembled to replace cage 11 (e.g., to change drug or when the drug is depleted) and/or filter 12 (e.g., if the filter becomes clogged). Pieces 6a and 6b can be attachable to one another via threaded connection or by other type of mechanical mechanism (e.g., interlocking tabs and slots). Catheter 7 is attached to an inlet in piece 6a; catheter 8 is attached to an outlet in piece 6b. Catheters 7 and 8 may be attached with epoxy or other adhesive. In other embodiments, barbed connectors may be employed. Clips and/or other locking mechanisms could also be used to retain catheters 7 and 8 to housing 6.

In at least some embodiments, osmotic pump 5 and drug/filter housing 6 are sized for implantation in specially prepared pockets in a patient's skull. Catheters 7 and 8 may be placed within grooves also prepared on the patient's skull.

In at least some embodiments, a subcutaneous (SC) port is implanted in a patient's body and placed into fluid communication with an implanted catheter and terminal component. The SC port includes an internal cavity or reservoir, which can be used to hold liquid or solid drug(s). A self-sealing elastomeric (e.g., silicone) septum covers the reservoir. The septum can also have a drug compatible fluoropolymer laminated lining to minimize drug adsorption. A non-coring needle may be inserted through the septum so as to introduce a fluid into the reservoir. That fluid can be a liquid formulated drug, or may be a liquid vehicle for dissolving a solid form drug already located within the reservoir cavity and delivering that dissolved drug to targeted tissue(s). In some embodiments, a liquid formulated drug is used as a vehicle to dissolve an additional solid-form drug contained in the reservoir.

Because an SC port is implanted beneath the skin, it may be more difficult to determine where the septum is located and to verify that a drug or vehicle is being injected into the port's reservoir. Accordingly, an optional electronic sensor can be placed inside of the reservoir so as to transmit a signal when a needle has penetrated the septum. A detector of this type is described in U.S. Pat. No. 6,962,580. Other systems for detecting and indicating the presence or absence of a needle within an SC port may utilize a conductive needle, a mechanical switch, a magnetic switch, a Hall Effect sensor, an electric field, a magnetic field, or an inductor. If a needle detection system is contained within the SC port, the detection system should be made from (or protected with) drug compatible materials. In still other embodiments, a pressure sensor is built into the SC port (or onto the needle injection system) to indicate a full SC port reservoir, and to avoid overfilling.

The drug-holding reservoir should be composed of (or coated with) a drug compatible material (e.g. stainless steel, titanium or drug compatible polymer). This material should also be biocompatible so as to prevent tissue rejection. The reservoir material should also withstand repeated refilling and dispensing of the drug and the potential corrosive effects of a drug-containing vehicle. The reservoir material must also be able to hold drug and remain implanted for an extended period of time without degradation. If an SC port is to be used for holding a drug in a solid state, the reservoir material should be compatible so that the drug does not stick to the reservoir walls. The reservoir surfaces that come in contact with a drug (whether solid or liquid) should be compatible so as not to adsorb any of the drug or be permeable to water/physiological fluids.

Examples of SC ports include those described in U.S. patent application Ser. No. 11/337,815 (titled "Apparatus and Method for Delivering Therapeutic and/or Other Agents to the Inner Ear and to Other Tissues" and filed Jan. 24, 2006), which application is incorporated by reference herein.

Figure 3:
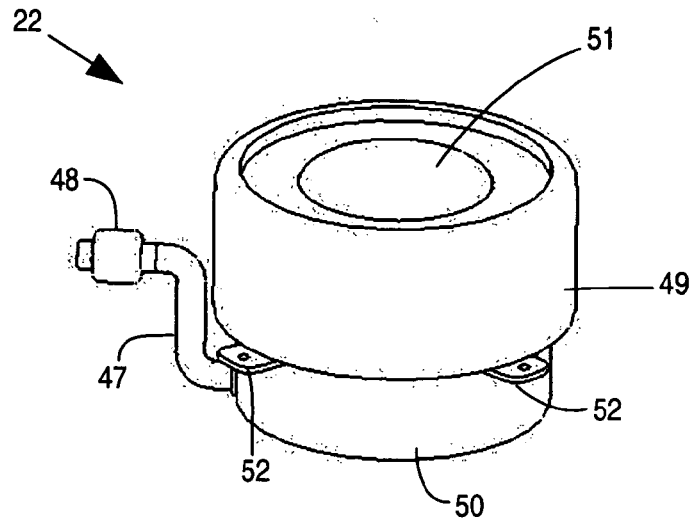
FIG. 3 is a perspective view of a subcutaneous (SC) port according to at least some embodiments.

FIG. 3 is an exterior perspective view of an SC port 22 according to at least some embodiments. SC port 22 includes an outlet tube 47 having an inline antibacterial filter 48. Outlet tube 47 can be connected (on the outlet side of filter 48) to a catheter, with the catheter then connected to a terminal component. A cap 49 is removable from a base 50 by a twist-off mechanism. A septum 51 is exposed in the top of cap 49. When cap 49 is removed septum 51 and a solid drug cartridge (not shown) inside SC port 22 can be replaced. Base 50 includes multiple projections 52 (ears in the embodiment shown) which can be used to secure SC port 22 in a patient's body. Holes in ears 52 can be used, e.g., as bone screw holes or as suture eyelets. Port 22 has a low profile to avoid the port erupting through a patient's skin.

Figure 4:
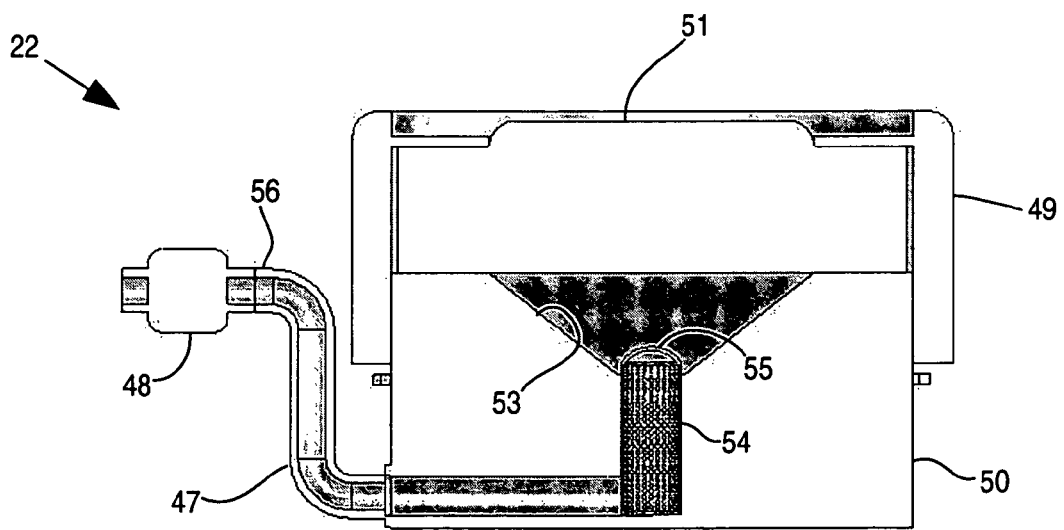
FIG. 4 is a cross-sectional view of the SC port of FIG. 3.

FIG. 4 is a cross-sectional view of SC port 22. Base 50 has an internal cavity 53 formed therein. Located in a well within cavity 53 is an optional cage 54 holding one or more solid drugs or other compound(s). Cage 54 includes a handle 55. Handle 55 permits simple removal (or replacement) of cage 54 when cap 49 and septum 51 have been removed. In other embodiments, the SC port includes a non-removable drug-holding cage; in at least some such embodiments, drug is replaced by opening the SC port and placing fresh solid drug into the non-removable cage. An antibacterial filter 48 may be attached to outlet tube 47 by threaded connection 56, thereby permitting removal and replacement of the antibacterial filter should it become clogged. In some embodiments, base 50 and cap 49 have mating threads permitting cap 49 to be screwed onto base 50. In still other embodiments, base 50 has a locking tab that fits within a groove of cap 49 (or vice versa). A threaded or tab/groove connection permits convenient removal of the cap 49 and replacement of septum 51 (e.g., if septum 51 has been excessively punctured by injection needles), cleaning of the port interior, or replenishment of solid drug cage 54.

In the embodiment of FIG. 4, as well as other embodiments where a solid drug is used, the drug can be melted, molded or compressed into a predetermined size and shape as dictated by the design of the SC port or the SC port cage (whether such cage is removable or non-removable). The drug-laden cage may then be installed at the time of device implantation. Alternatively, the drug cage could be installed at the time of device manufacture or at the time of device shipment from the manufacturer/distributor. In embodiments where the drug cage is removable, use of a drug cage permits replenishment of a drug through a minor surgical procedure to open a drug-cage-containing compartment in the SC port, reservoir, pump or other components. In at least some embodiments where the drug cage is not removable, the drug is replenished by removal of the entire capsule or port.

Figure 5:
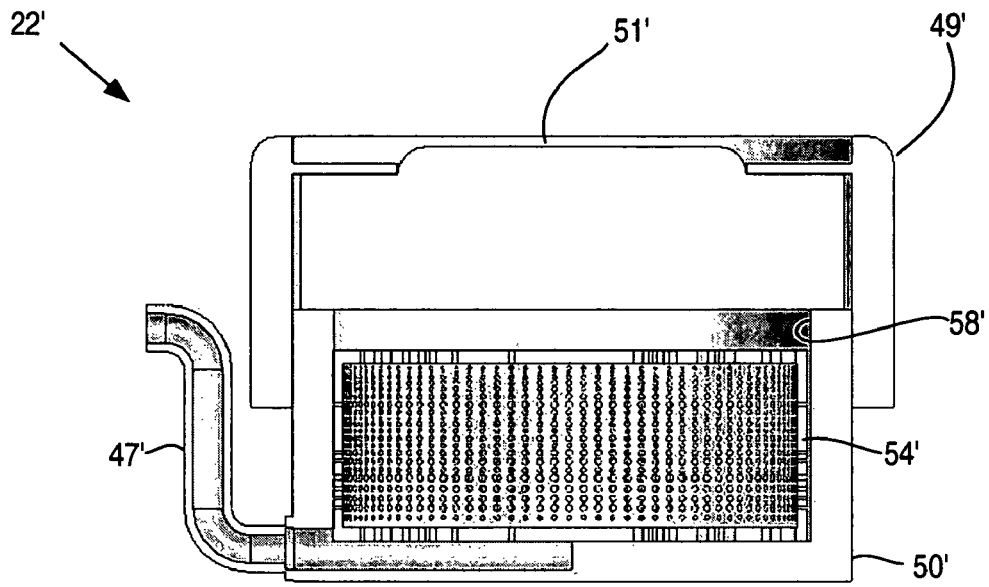
FIG. 5 is a cross-sectional view of an SC port according to another embodiment.
Figure 6:
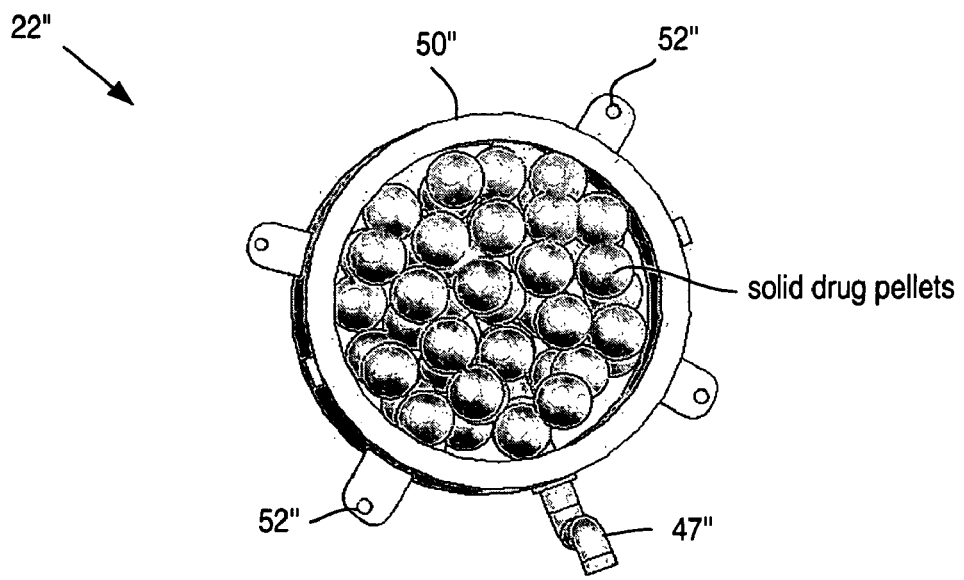
FIG. 6 is a perspective view of an SC port containing solid drug pellets.

FIG. 5 shows a cross-sectional view of an SC port 22' according to another embodiment. Cylindrical drug cage 54' fills up the entire drug reservoir except for a small space 58 at the top. There is sufficient room in and around cage 54' to allow vehicle to circulate around the solid drug and then exit through an outlet catheter. Components on SC port 22' and SC port 22 (FIGS. 3 and 4) with similar functions have the same reference numbers in the two figures, except for the inclusion of an apostrophe in the reference numbers of FIG. 5. FIG. 6 shows an SC port 22" according to another embodiment. The septum and cover of port 22" are removed to show the interior cavity of port 22" filled with solid drug pellets in lieu of a porous drug-holding cage. Components of SC port 22" and of SC port 22 (FIGS. 3 and 4) with similar functions have the same reference numbers in the two figures, except for the inclusion of two apostrophes in the reference numbers of FIG. 6.

In at least some embodiments, ports such as are shown in FIGS. 3-6 are sized for implantation in specially prepared pockets in a patient's skull.

Figure 7:
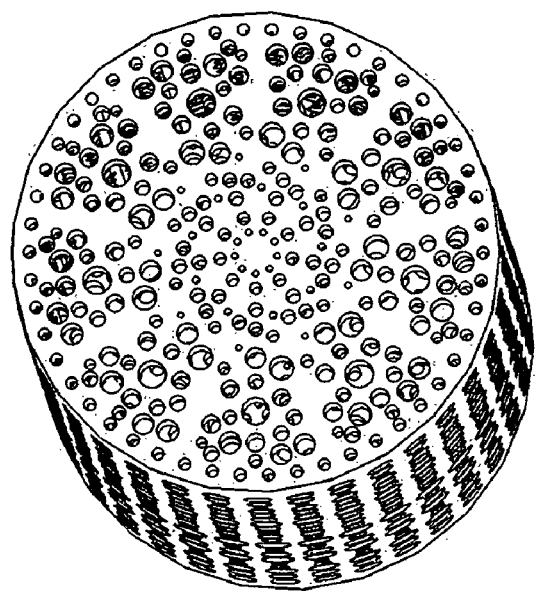
FIG. 7 is a perspective view of a drug cage according to at least some embodiments.
Figure 8:
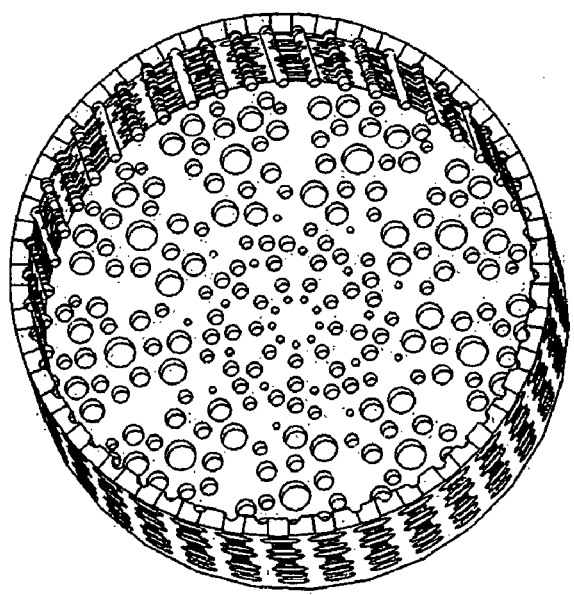
FIG. 8 is a cross-sectional view of the cage of FIG. 7.

FIG. 7 is an exterior perspective view of a solid drug holding cage such as may be used in the embodiments of FIGS. 1-5. The cages used in these (and other) embodiments are similar, but have dimensions that correspond to the cavity of an SC port or drug/filter housing for which a given cage is intended. FIG. 8 is a cross sectional view of the cage in FIG. 7. The solid drug cage is a container designed to hold one or more solid drugs and allow a liquid vehicle to flow through the container and around the drug(s), thereby eroding some of the solid drug(s). The eroded and now dissolved portion of the drug(s) is then carried to the target tissue by the eroding vehicle. There is sufficient room in and around the cage to allow the vehicle to circulate around the solid drug(s). As shown in FIG. 8, one embodiment of the cage may incorporate grooves cut into the inner wall, providing channels for fluid flow through the cage. In some embodiments, a solid drug is melted, molded or compressed into a predetermined size and shape dictated by the size of the cage. This solid section of drug may have one or more holes drilled through it to allow vehicle to pass through. In other embodiments the drug cage may be filled with multiple smaller solid drug pellets (similar to the pellets shown in FIG. 6). In such a case, the vehicle is able to pass through the spaces between the pellets, dissolving drug along the way. In some embodiments, the solid drug cage is designed to be removable, and may include, for convenience, an optional handle as shown in FIG. 4. Use of the drug cage permits replenishment of a drug through a minor surgical procedure to open the compartment in an SC port or drug/filter housing where the cage is located. The solid drug cage is preferably composed of (or coated with) a drug compatible/biocompatible material (e.g. stainless steel, titanium, or drug compatible polymer). The material is preferably one to which the intended drug will not adhere. The sizes of the holes in the cage may also be varied based on the drug to be held within the cage. For example, a cage for holding a monolithic piece of solid drug may have larger holes than a cage for holding solid drug in a powder or pellet form. Cage hole size may also vary based on the solubility of an intended drug and/or the desired concentration of drug within a liquid vehicle. In some embodiments, the drug cage is not removable.

As shown above, antibacterial filters may be placed on the outlet of an SC port or in an inline drug/filter housing. In other embodiments, an antibacterial filter may be included in other locations (e.g., within an SC port cavity, in a separate inline housing without a drug cage, etc.). At least one antibacterial filter is preferably included in the fluid path before the drug is delivered to the patient. The antibacterial filter is constructed from porous stainless steel, titanium or biocompatible and drug compatible polymeric materials. Fabrication of antibacterial filters suitable for this kind of system has been described in detail in the above mentioned U.S. patent application Ser. No. 11/337,815. An antibacterial filter is a preferred component and provides safety advantages. If bacteria is introduced into the delivery system and reaches a target tissue, the patient could suffer from bacterial meningitis or other serious infections. An in-line filter having pores of size 0.2 µm or less can prevent bacteria from reaching the patient. Three-dimensional porous metal antibacterial filters are preferred because of dimensional strength and compact size.

Numerous types of catheters can be used in various embodiments. In at least some embodiments, implanted catheters are formed from drug- and biocompatible materials such as fluoropolymers (e.g., PTFE, FEP, ETFE and PFA), silicone rubber, PVC, PEEK, polyimide and polyurethane. The precise compound selected for a catheter will depend on the drug to be delivered. Examples of some catheters which can be used are described in the aforementioned U.S. patent application Ser. No. 11/337,815. Single-lumen and multi-lumen catheters can be used. The selection and assembly of appropriate catheters and connectors is within the ability of persons skilled in the art once such persons are provided with the information described herein.

Figure 9A:
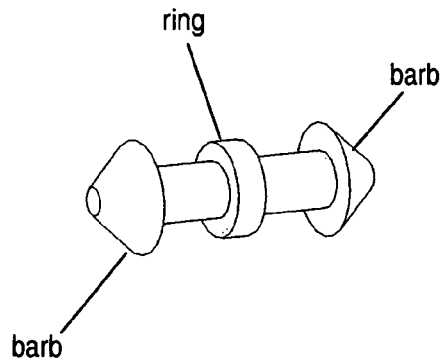
FIGS. 9A-9C show tubing connectors according to at least some embodiments.
Figure 9B:
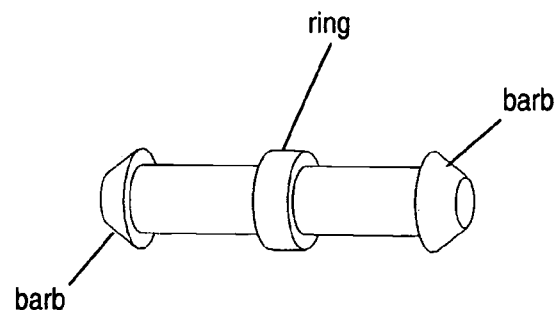
Figure 9C:
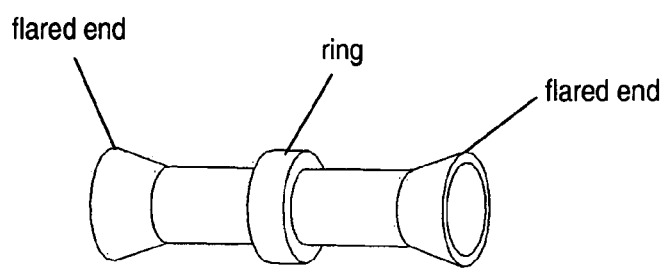

FIGS. 9A-9C are perspective views of several of the connectors which can be used in various embodiments to join a catheter to a terminal component, to another catheter, to an osmotic pump or an SC port, or to another component. The connectors have barbed or flared ends to aid in a tight connection. A ring located midway along the connector length acts as a tubing insertion stop to ensure that a catheter or other component on each side of the connector has sufficient engagement to form a tight connection with the connector piece. The connectors of FIGS. 9A-9C can be formed from bio- and drug-compatible materials such as titanium, stainless steel and fluoropolymers. The connectors of FIGS. 9A-9C have dimensions to facilitate a firm connection between a catheter and a terminal component. For example, the terminal component could be a cochlear implant electrode having a stylet tube hole. In such case, the connector is inserted into the stylet tubing hole within the cochlear implant electrode. As other examples, a connector could be inserted into needle assembly for delivery of a drug to a tumor, arthritic joint, brain, liver or other tissue.

Figure 10:
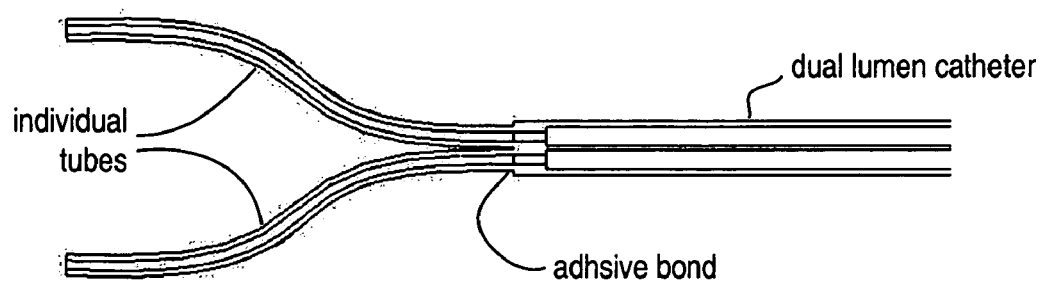
FIGS. 10 and 11 show connection of two tubes to a double-lumen catheter.
Figure 11:
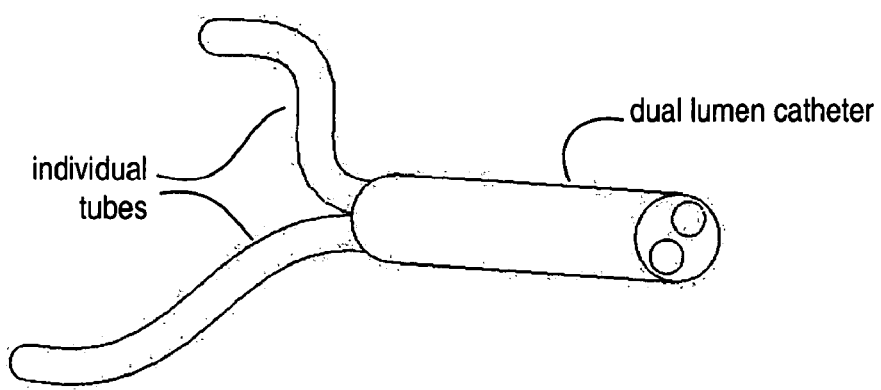

In some embodiments, multiple tubes merge to form a "Y" shaped connection, where the two separate single-lumen tubes merge into a single dual-lumen tube. For example, one tube may be attached to a first SC port and another tube may be attached to a second SC port (or to an osmotic pump and drug/filter housing), thereby permitting multiple drugs to be mixed at the time of delivery. The first and second lumens of the dual-lumen tube remain in fluid communication with the respective single lumens of each individual tube. In one embodiment, the two individual tubes are attached and sealed to the dual lumen tubing by insertion into the circular holes of the lumens and application of cyanoacrylate or other adhesives suitable for the intended purpose and approvable by regulatory agencies. FIGS. 10 and 11 are cross-sectional and perspective views, respectively, of such a connection. In other embodiments a metal or plastic connector may be used to join the dual lumen tubing with the two individual tubes. In at least one embodiment, bifurcated tubing has a unitary construction and is extruded as one piece. This can be manufactured using a special extruder die similar to that described in U.S. Pat. No. 5,945,052. In alternative embodiments the bifurcated tubing may be molded to provide a unitary construction. These multi-lumen and bifurcated multi-lumen tubings offer flexibility for multiple simultaneous purposes such as adding drug, withdrawing excess fluid, sampling physiological fluids, placing a biosensor at the target tissue, electrical stimulation, electrical sensing, etc. Although FIGS. 10 and 11 show catheters with dual lumens, catheters having three or more lumens could also be used in alternate embodiments. Some or all of those lumens can be connected to a separate port, osmotic pump, etc.

A catheter can be permanently connected to an SC port or other component, or can be detachable and re-attachable. In some embodiments, a clip or other locking mechanism may be used. An example of a snap/lock fitting is described in U.S. Pat. No. 4,929,236. Other examples of the locking fittings include a catheter/connection that includes a screw connection, a twist-lock or a tab-lock. These and other types of connectors can be used with single or multiple lumen catheters. In some embodiments, two or more SC ports (or osmotic pumps) are connected to multilumen tubing (or to separate tubing) so as to allow simultaneous administration of multiple fluids to a target tissue, or to allow one device to withdraw fluid while the other is delivering fluid.

As indicated above, a solid drug may sometimes be used in a drug delivery system that does not include an implanted pump. This approach allows an SC port containing the solid drug to be implanted within the patient. A fluid path is formed from the SC port cavity, through a catheter lumen, to an outlet of a terminal connector. An external pumping system loaded with a sterile vehicle is then periodically attached to the port with an infusion set. Vehicle delivered from the external pumping system is then used to dissolve a portion of the drug. The vehicle and drug then exit through an outlet of the SC port and flow through the fluid path for delivery to a target tissue. This approach avoids the complexity of an implanted pumping system and the potential of complex repairs should there be a mechanical or electronic failure.

Figure 12:
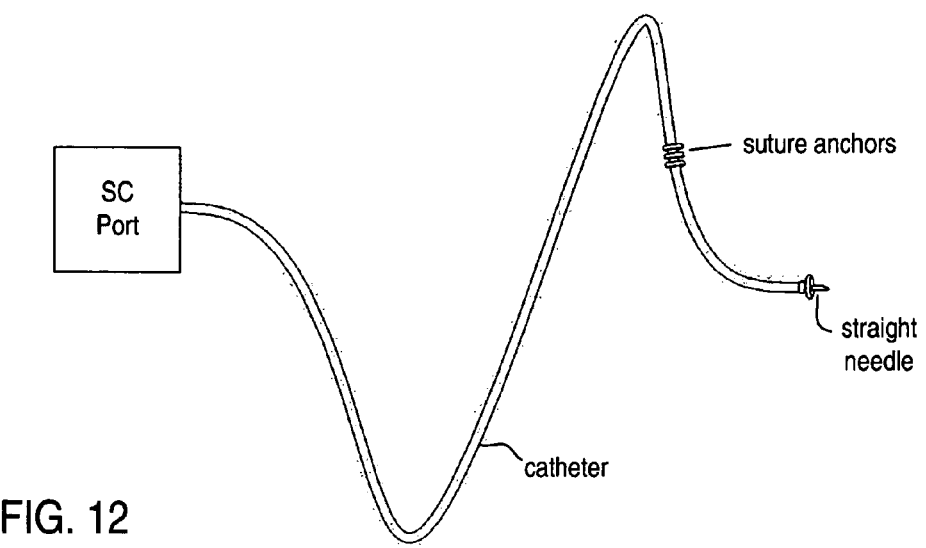
FIG. 12 is a drawing of an SC port, catheter and straight needle.

FIG. 12 shows one arrangement implementing the above-described approach. An SC port (shown in block diagram form) is connected to a catheter, which catheter is also implanted inside the patient's body. A straight needle assembly is attached to a distal end of the catheter. A flange or other type of needle stop prevents over insertion of the needle into the target tissue. Optional suture anchors near the straight needle provide a means of securing the catheter in place. As with other configurations described herein, the configuration of FIG. 12 can be employed to deliver therapeutics, immunotherapeutics and vaccines to lymph nodes, tumors or other tissue. The SC port could contain a solid drug which is then dissolved by a sterile vehicle (e.g., saline, Ringer's solution, artificial perilymph, etc.) introduced into the port from an external pump. Alternatively, the SC port can be "empty," and with an external pump providing both the drug and sterile vehicle into the cavity of the SC port from an external syringe or other reservoir. Drugs and other agents that can be introduced in this manner include plasmids for immunotherapy, peptides, proteins, cytotoxics, immunoprotectants, steroids (such as triamcinolone acetate, dexamethasone and methylprednisolone) and other therapeutics to patients in need of intermittent or short term therapy for which a needle injection is insufficient to provide practical therapy.

Figure 13:
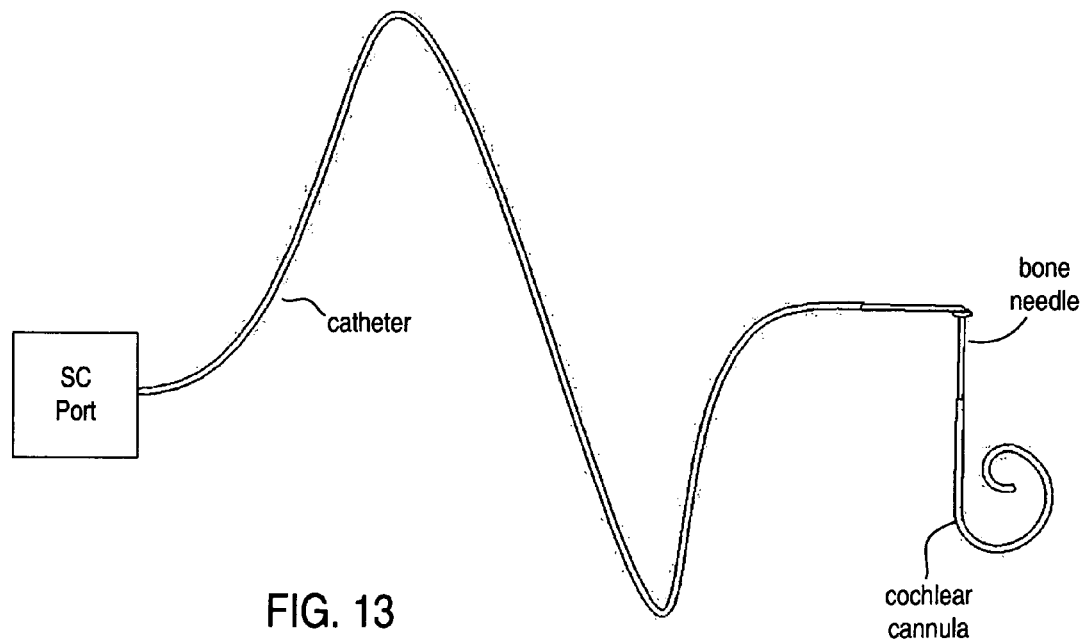
FIG. 13 is a drawing of an SC port, catheter, bone needle and cochlear cannula.

As an alternative to the arrangement shown in FIG. 12, the SC port could be connected to a bone needle, to a cochlear implant electrode, or to another type of terminal component. For example, FIG. 13 shows an SC port and catheter connected to a bone needle, with the bone needle attached to a cochlear cannula for delivery of drugs to the cochlea. The cochlear cannula is a small tube which can be inserted into a patient's cochlea. The cochlear cannula may include one or more holes for release of the delivered drug at multiple locations. In variations on the embodiment of FIG. 13, a connector piece (such as is shown in FIGS. 9A-9C) is substituted for the bone needle. In still other variations, a biosensor can be combined with the cochlear cannula. Of course, an implanted osmotic pump may be used with a catheter and cochlear cannula in alternate embodiments without connecting through a straight, bone or other type of needle. In these embodiments the catheter, cochlear cannula or cochlear electrode may be connected to a catheter with one of the connectors in 9A-C.

Figure 14:
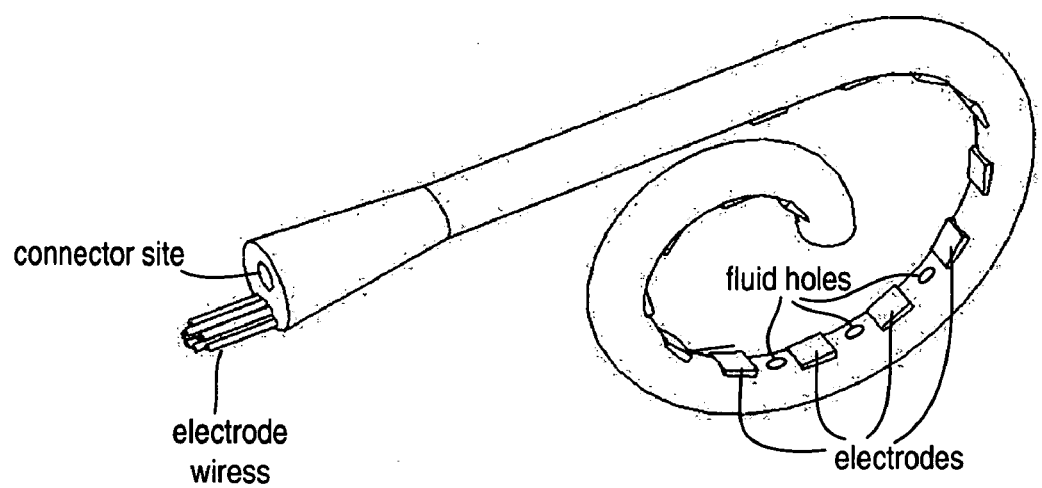
FIG. 14 is a drawing of a cochlear implant electrode.

FIG. 14 shows a cochlear implant electrode which can be used in various embodiments (including embodiments with and embodiments without an implanted osmotic pump). Similar to conventional cochlear implant electrodes, the cochlear implant electrode of FIG. 14 includes electrodes to stimulate the cochlea of a hearing impaired patient. However, the cochlear implant electrode of FIG. 14 further includes drug delivery holes which are in fluid communication with an internal conduit; that conduit terminates at a connection site to which a catheter can be connected (e.g., with a connector such as shown in FIGS. 9A-9C). The drug delivery holes in the cochlear implant electrode of FIG. 14 are on the same side as the electrodes. In other embodiments, the drug delivery holes could be located on other sides (e.g., on an opposite side).

Figure 15:
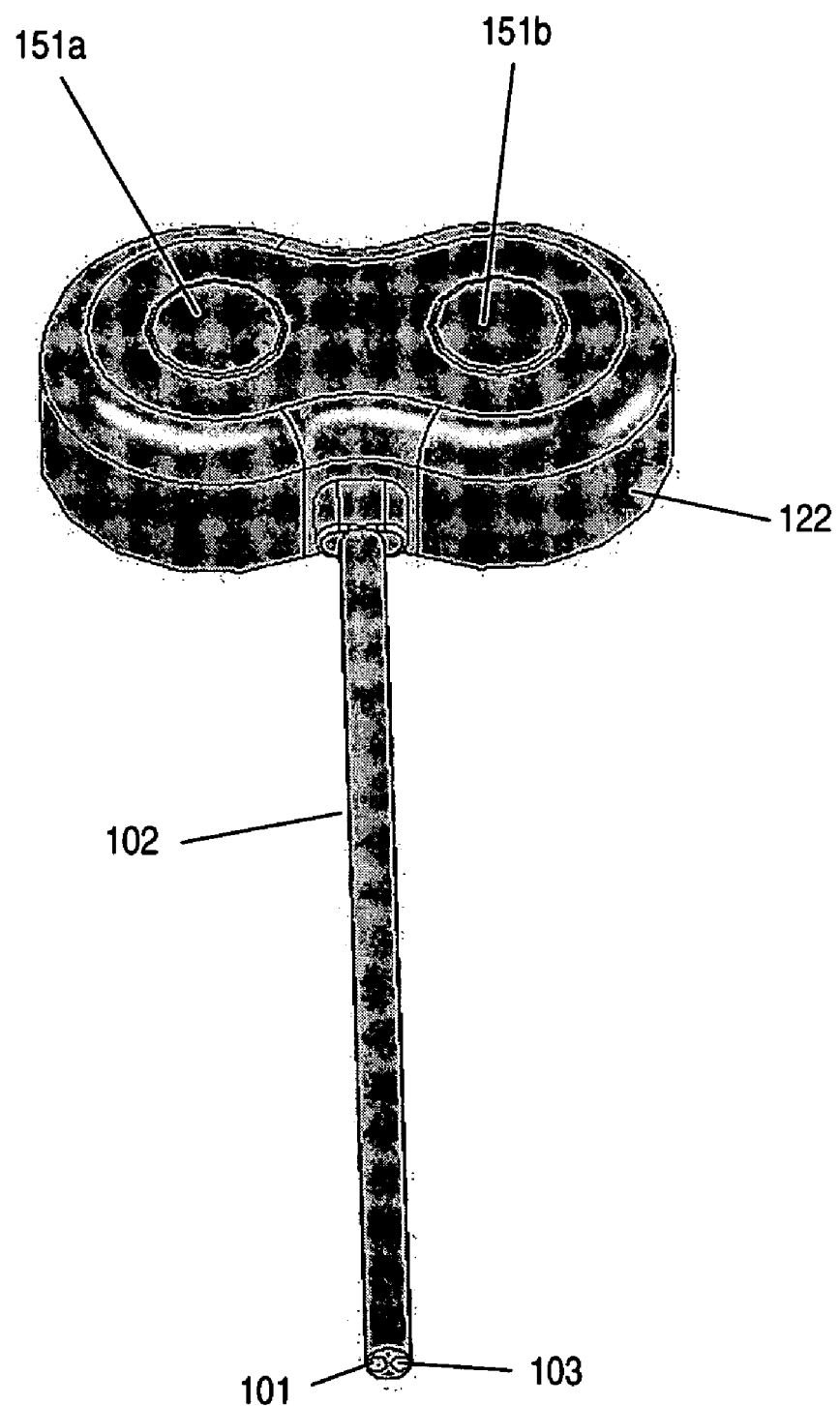
FIG. 15 is a perspective view of an SC port according to another embodiment.
Figure 16:
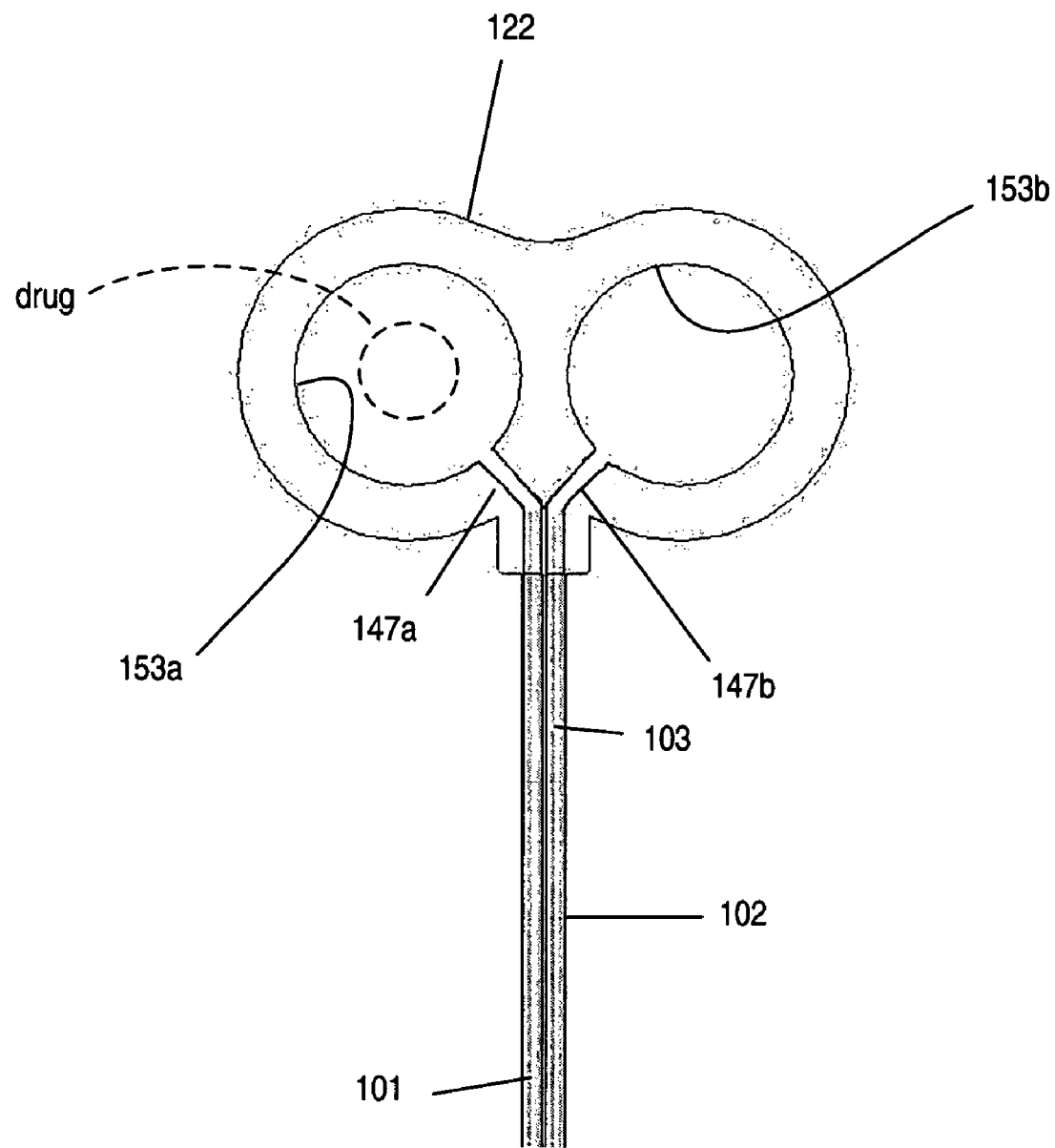
FIG. 16 is a cross sectional view of the SC port of FIG. 15.

FIG. 15 is a perspective view of an implantable SC port 122 according to another embodiment of the invention. FIG. 16 is a cross sectional view SC port 122. SC port 122 includes two cavities 153a and 153b (FIG. 16) which are covered by two septa 151a and 151b (FIG. 15). Cavity 153a is in fluid communication (via an outlet tube 147a) with a lumen 101 of a dual lumen catheter 102. Cavity 153b is in fluid communication (via an inlet tube 147b) with a lumen 103 of dual lumen catheter 102. The embodiment of FIGS. 15 and 16 permits flushing of a target tissue, with one side of the port (septum 151a, cavity 153a and outlet 147a) receiving fluid from another source (e.g., an external pump) and with the other side (septum 151b, cavity 153b and inlet 147b) used to withdraw fluid from the target tissue. In some embodiments, cavity 153a may also contain a drug and/or an antibacterial filter (not shown), or an antibacterial filter may be placed within outlet 147a. In the embodiment of FIGS. 15 and 16, a single cap holds septa 151a and 151b over cavities 153a and 153b. In other embodiments, separate caps may be employed. In still other embodiments, one side is covered with a removable cap and the other side is covered with a nonremovable cap. Preferably, the side receiving fluid for transmission to the target tissue also includes an antibacterial filter (not shown) in the fluid transmission pathway.

Using the embodiment of FIG. 15, one lumen of a multi lumen catheter is usable to prime the SC port and catheter, and/or to wash the tissue site. The other lumen is used for removing the excess fluid. If a system has a high dead volume, for example, the system can be flushed by using the multi-lumen tubing. The excess fluid entering the tissue will drain out the second lumen in the tube to avoid over pressure at the tubing head. Alternatively, the tissue at the tubing head may be washed with injected fluid until the dead volume is exchanged, the undesired fluid is flushed from the system, and the tissue is ready to receive the drug. This would also be useful in cases where a drug is unstable and requires replacement with fresh drug.

In at least some embodiments, a drug delivery system such as is described above in connection with any of FIGS. 1-6 and 12-16 is placed in the periosteum of the mastoid bone, with a cannula from the drug delivery system located in the periosteum (between the skin and the mastoid bone) or within a groove carved on the mastoid bone. The catheter extends to the temporal bone and joins a cochlear implant electrode just before the implant penetrates the temporal bone into the cochlea. In order to be implantable within a patient, components of the system are formed from (or are encased within) biocompatible materials. Drug-contacting surfaces of components are, in at least some embodiments, formed from materials which are compatible with drugs having a pH between 4-9. The components (or packages into which the components have been placed) may be attachable to other skull locations (e.g., placed in a predrilled pocket and secured with bone screws), to muscle or to other tissues.

Figure 17A:
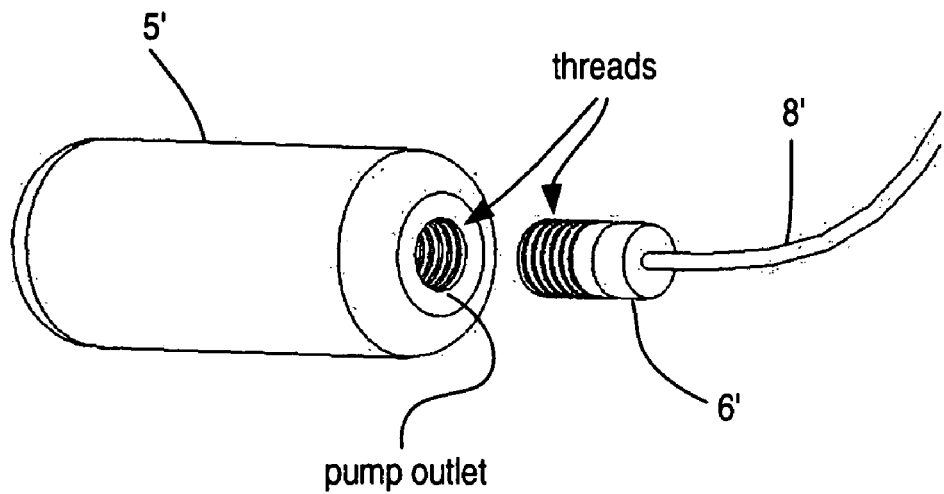
FIGS. 17A and 17B show an implantable drug delivery system according to at least some additional embodiments.
Figure 17B:
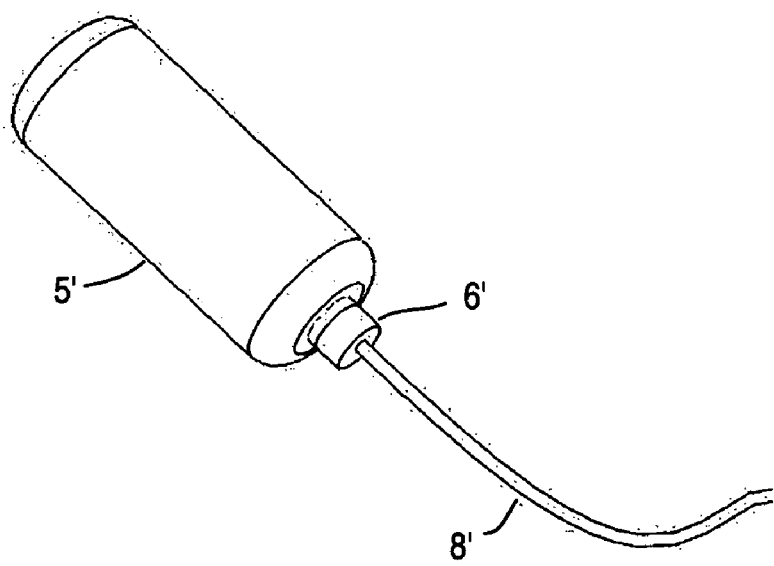

FIGS. 17A and 17B show a drug delivery system according to another embodiment. Osmotic pump 5' is similar to osmotic pump 5 of FIG. 1, except that the outlet of pump 5' is somewhat enlarged and has internal threads. Drug/filter housing 6' is similar to housing 6 of FIGS. 1 and 2. However, housing 6' has external threads corresponding to the internal threads on the outlet of pump 5'. As shown in FIG. 17B, this facilitates a direct attachment between pump 5' and housing 6', thereby avoiding the need for one of the catheters (i.e., catheter 7) shown in FIG. 1. An inlet to housing 6' (similar to the inlet of housing 6 connected to catheter 7 in FIG. 2) is placed into fluid communication with the outlet of pump 5'. The dimensions of the housing 6 will depend on the drug(s) being delivered and the surface area required to provide a desired concentration of the drug(s).

The configuration of FIGS. 17A-17B allows periodic removal of housing 6' from pump 5' for replacement of drug and/or a filter within housing 6'. In variations on the embodiment of FIGS. 17A-17B, other types of connection mechanisms (e.g., locking tab and groove) between pump 5' and housing 6' are employed. In still other variations, housing 6' is permanently attached (e.g., with adhesive) to pump 5'.

Figure 18:
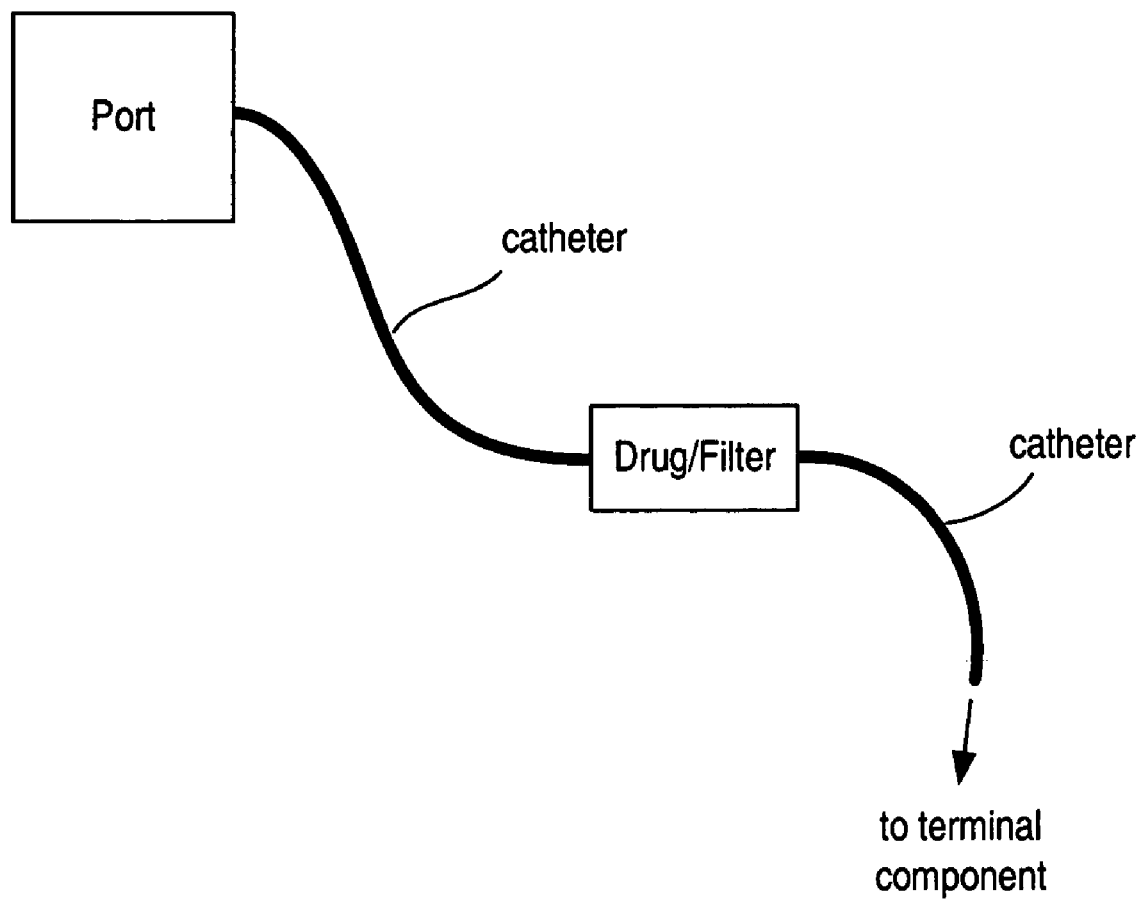
FIG. 18 is a schematic drawing of an implantable drug delivery system according to another embodiment.

FIG. 18 is a schematic block diagram of a fluid delivery system according to additional embodiments. The embodiment of FIG. 18 combines features of the SC port embodiments (e.g., as described in connection with FIGS. 3-6, 12, 13 and 15) with a separate drug/filter housing (such as housing 6 in FIGS. 1-2). In the embodiment of FIG. 18, a solid drug is placed in a separate housing instead of within a cavity of the SC port. A catheter connects an outlet of the SC port and an inlet of the drug/filter housing, with another catheter connecting the drug/filter housing outlet to a terminal component (not shown). The internal cavity of the SC port, the lumens of the catheters, the internal cavity of the drug/filter housing and the terminal component form a fluid path. A vehicle (e.g., saline, Ringer's solution, artificial perilymph) is introduced through a septum of the SC port via an infusion set coupled to an external pump and fluid supply. Fluid from the external supply flows from the SC port, through the catheters and housing, and to the terminal component. As that fluid flows, solid drug in the housing is dissolved and delivered to the target tissue(s) in which the terminal component is implanted.

Systems such as those described above can be used to administer any of a wide variety of drugs to treat and/or diagnose numerous conditions. The following are provided by way of example, and not by way of limitation, to illustrate some such uses.

Systems such as are described herein can be used to deliver therapeutics to the inner ear to treat hearing-related disorders and other ailments such as tinnitus, infections of the inner ear, inflammatory diseases, inner ear cancer, acoustic neuroma, acoustic trauma, Ménière's Disease and the like. In some cases, the drugs can be applied via a modified cochlear implant electrode such as is shown in FIG. 14. In other cases (i.e., where a cochlear implant electrode is not desired) a drug might be delivered directly to the cochlea through a hole in the bone (either in the basal turn of the cochlea with a short needle or cannula or further into the cochlea with a cannula with one or more holes in the appropriate locations).

Other examples include drug delivery to the brain for treatment of chronic pain, migraines and various neurological disorders such as Parkinson's disease, epilepsy, schizophrenia or Alzheimer's disease. Dopamine agonists can be used to stimulate dopamine receptors in the substantia nigra, the part of the brain in which Parkinson's disease is thought to originate. Drugs that block dopamine receptors, such as chlorpromazine (Thorazine), can be delivered in the basal ganglia to treat schizophrenia.

Other applications for direct drug delivery include:

Hormones could be delivered to the pituitary, hypothalamus or pineal for treatment of various disorders.

Taurine is a neuroprotective substance that can be used for various therapeutic applications, such as treating stroke and various seizure disorders, such as epilepsy. However, taurine does not cross the blood brain barrier effectively. Direct delivery of taurine by injection at the focal point of stroke, traumatic brain injury or seizure would solve this problem and render feasible the therapeutic use of taurine.

Delivery of various protein hormones is hampered because of rapid degradation by proteases prior to arrival at the site of action. Use of systems such as those described herein could address this problem. This could permit, e.g., use of endorphins for the treatment of localized pain to avoid the addictive properties of other non-protein drugs (e.g., morphine).

Tissue-specific delivery of necessary hormones could enhance specificity and therapeutic efficacy. This could include delivery of atrial natriuretic factor (ANF) or atriopeptin to outer adrenal cells; arginine vasopressin to the distal kidney tubule; cholecystokinin to stimulate gallbladder contraction and bile flow or to increase secretion of pancreatic enzymes; erythropoietin to bone marrow to stimulate hemoglobin synthesis; relaxin to the placenta to reduce myometrial contractions; and follicle-stimulating hormone to testis and ovaries to enhance fertility.

Required enzymes could be delivered to necessary tissues to treat inborn errors of metabolism, such as delivery of hexosaminidase A across the blood brain barrier and to the macula for the treatment of Tay-Sachs disease. The enzyme glutamate decarboxylase could also be delivered to the focal point of brain injury to convert glutamate, which induces neuron apoptosis, to $\gamma$-amino butyrate, which is neuroprotective.

Gene therapy would be most efficient by delivery of deficient genes to the tissues lacking them. For example, the genes for adenosine deaminase or glucocerebrosidase could be delivered directly to the thymus, spleen or bone marrow to treat adenosine deaminase deficiency or Gaucher's disease, respectively. Similarly, cell replacement therapy with either stem cells or progenitor cells of the type required could be delivered directly to the target tissue. This could include delivery of progenitor cells for the substantia nigra for the treatment of Parkinson's disease or progenitor cells for the islet $\alpha$, $\beta$, $\delta$ and/or PP cells of the pancreas for the treatment of diabetes.

Systems such as are described herein can be used to deliver drugs to various regions of the brain for treatment of chronic pain, mental illnesses and other diseases of the central nervous system. In some cases, drugs can be delivered to the brain through a hole in the skull using a bone needle.

Systems such as are described herein can be used to deliver drugs to a lymph node (using, e.g., a straight needle) for treatment of autoimmune diseases with therapeutics designed to modulate the immune response or improve the $T_H1/T_H2$ balance in allergic conditions. Such systems can also be used to treat allergies to bee venom, dust, ragweed, cats, food, etc.

Systems such as are described herein can be used to deliver drugs (using, e.g., a straight or other type of needle) to a cancer tumor so as to locally treat with a cytotoxic or an anticancer prodrug designed to overcome the tumor or drug resistance of the tumor. A system such as those described above could also allow the prophylactic or immunotherapy treatment of a cancer. In some embodiments, for example, immunotherapeutics for cancer (anti-cancer "vaccines") are injected into a lymph node (e.g., the inguinal lymph node). Cancer immunotherapeutics are described, for example, in US 2005/0130920, US 2005/0013812, US 2004/0223949, US 2004/0209836, US 2004/0156858, and US 2004/0091995 Preferred cancer immunotherapeutics can include one or more DNA plasmid(s) appropriately configured to express one or more antigenic epitope(s) to train the T-cells to recognize the same epitope(s) on target cancer cells. The so trained T-cells then leave the lymph node and kill (bind to or attack) the cancer cells which have the same epitopes. The therapy also results in the training of B-cells to differentiate and produce antibodies recognizing the same epitope(s) which subsequently bind/neutralize the target protein or cell. During the course of therapy, other materials may be injected, such as mixtures of peptide or protein epitopes which can further enhance the antibody titer and provide a better overall therapeutic response. In other embodiments, cancer immunotherapeutics or chemotherapeutics can be injected directly into tumors or in their vicinity.

Systems such as those described above could be used to deliver any of the compounds described in the above-mentioned U.S. patent application Ser. No. 11/337,815, for treatment of the conditions described therein (or treatment of other conditions).

Other uses include delivery of plasmids for immunotherapy or genetic therapy (gene therapy); delivery of peptides, proteins, steroids (for example, triamcinolone acetate, dexamethasone and methylprednisolone) and other anti-inflammatory therapeutics; and delivery of cytotoxics and other therapeutics.

The above are only examples. The possible applications for direct drug delivery are far too numerous to list exhaustively herein.

Numerous characteristics, advantages and embodiments of the invention have been described in detail in the foregoing description with reference to the accompanying drawings. However, the above description and drawings are illustrative only, and the invention is not limited to the illustrated embodiments. Various changes and modifications may be effected therein by one skilled in the art without departing from the scope or spirit of the invention. Although example materials and dimensions have been provided, the invention is not limited to such materials or dimensions unless specifically required by the language of a claim. The elements and uses of the above-described embodiments can be rearranged and combined in manners other than specifically described above, with any and all permutations within the scope of the invention. As used herein (including the claims), "in fluid communication" means that fluid can flow from one component to another; such flow may be by way of one or more intermediate (and not specifically mentioned) other components; and such may or may not be selectively interrupted (e.g., with a valve).

As also used herein (including the claims), "coupled" includes two components that are attached (movably or fixedly) by one or more intermediate components.

The invention claimed is:

1. An apparatus for delivery of one or more drugs to a target tissue, comprising:
    a subcutaneously-implantable osmotic pump having an outlet;
    a subcutaneously-implantable housing having an inlet in fluid communication with the pump outlet, an internal cavity in fluid communication with the inlet and containing one or more solid drugs, and an outlet in fluid communication with the cavity, wherein the housing further includes first and second sections, and wherein the first and second sections are non-destructively removable from one another to expose the cavity;
    a catheter having a lumen in fluid communication with the housing outlet; and
    a terminal component in fluid communication with the catheter lumen and configured for implantation in the target tissue, wherein the terminal component comprises a bone needle configured for insertion through a bone into the cochlea of a human implantee and being bent so as to allow complete implantation below the skin of the implantee, the bone needle further including an insertion stop formed from a biocompatible porous material configured for integration into the bone of the implantee.

2. The apparatus of claim 1, wherein the housing is non-destructively removable from the pump.

3. The apparatus of claim 2, wherein the pump outlet and housing inlet are connected by a second catheter.

4. The apparatus of claim 1, wherein the housing further includes an antibacterial filter positioned in a fluid path between the one or more solid drugs and the housing outlet.

5. The apparatus of claim 1, wherein the one or more solid drugs are contained within a removable cage located within the housing cavity.

6. The apparatus of claim 5, wherein the housing further includes an antibacterial filter positioned in a fluid path between the one or more solid drugs and the housing outlet.

7. The apparatus of claim 1, wherein the one or more solid drugs are contained within a non-removable cage located within the housing cavity.

8. The apparatus of claim 5, wherein the one or more solid drugs contained within the removable cage are monolithic.

9. The apparatus of claim 5, wherein the one or more solid drugs contained within the removable cage are in powder form.

10. The apparatus of claim 5, wherein the one or more solid drugs contained within the removable cage are in the form of pellets.

* * * * *